US008148415B2

(12) United States Patent
Potter et al.

(10) Patent No.: US 8,148,415 B2
(45) Date of Patent: Apr. 3, 2012

(54) SULFAMIC ACID ESTER COMPOUNDS USEFUL IN THE INHIBITION OF STEROID SULPHATASE ACTIVITY AND AROMATASE ACTIVITY

(75) Inventors: Barry Victor Lloyd Potter, Slough (GB); Michael John Reed, Slough (GB); Lok Wai Lawrence Woo, Slough (GB); Atul Purohit, Slough (GB); Christian Burbert, Slough (GB); Paul Michael Wood, Slough (GB); Oliver Brook Sutcliffe, Slough (GB)

(73) Assignee: Sterix Limited, Berkshire (GB)

( * ) Notice: Subject to any disclaimer, the term of this patent is extended or adjusted under 35 U.S.C. 154(b) by 0 days.

(21) Appl. No.: 11/603,941

(22) Filed: Nov. 22, 2006

(65) Prior Publication Data
US 2007/0213383 A1 Sep. 13, 2007

Related U.S. Application Data

(63) Continuation-in-part of application No. PCT/GB2005/001985, filed on May 19, 2005.

(30) Foreign Application Priority Data

May 24, 2004 (GB) .................................. 0411562.2

(51) Int. Cl.
*A61K 31/4192* (2006.01)
*A61K 31/4196* (2006.01)
*C07D 249/04* (2006.01)
*C07D 249/08* (2006.01)

(52) U.S. Cl. ..................................... 514/383; 548/268.6
(58) Field of Classification Search ................ 548/268.6
See application file for complete search history.

(56) References Cited

U.S. PATENT DOCUMENTS
2006/0241173 A1 * 10/2006 Reed et al. ..................... 514/456

FOREIGN PATENT DOCUMENTS
| EP | 0 641 785 | 3/1995 |
| EP | 1 193 250 | 4/2002 |
| EP | 1 544 195 | 6/2005 |
| WO | WO 03/045925 | 6/2003 |
| WO | WO 03045925 A1 * | 6/2003 |

OTHER PUBLICATIONS

Cancer and Metastasis Reviews (1998), 17(1), 91-106.*
Science (1999), vol. 286, 531-537.*
Cancer [online], [retrieved on Jul. 6, 2007], Retrieved from the Internet, URL; http://www.nlm.nih.gov/medlineplus/cancer.html>.*
Cancer [online], [retrieved on Jul. 6, 2007], Retrieved from the Internet, URL; http://en.wikipedia.org/wiki/Cancer>.*
Hatem A.M. Hejaz, et al., Synthesis, In Vitro and In Vivo Activity of Benzophenone-Based Inhibitors of Steroid Sulfatase, Bioorganic & Medicinal Chemistry (2004) vol. 12, p. 2759-2772.
L.W. Lawrence Woo, et al., First Dual Aromatase-Steroid Sulfatase Inhibitors, J. Med. Chem. (2003) vol. 46, p. 3193-3196.
Reed, et al., Steroid Sulphatase: Molecular Biology, Regulation, and Inhibition, Endocrine Reviews, Apr. 2005, 26(2), 171-202.

* cited by examiner

*Primary Examiner* — Shawquia Young
(74) *Attorney, Agent, or Firm* — Frommer Lawrence & Haug LLP; Sandra Kuzmich, Esq.

(57) ABSTRACT

The present invention relates to steroid sulphatase and/or aromatase inhibitors of Formula III or Formula IV, wherein A is selected from H, OH, halogen and hydrocarbyl; D, E and F are each independently of each other an optional linker group; P, Q and R are independently of each other a ring system, wherein $R^4$ and $R^5$ are independently selected from H, alkyl, cycloalkyl, alkenyl, acyl and aryl, or combinations thereof, or together represent alkylene, wherein the or each alkyl or cycloalkyl or alkenyl or optionally contain one or more hetero atoms or groups, and which can be used in medicine.

17 Claims, 2 Drawing Sheets

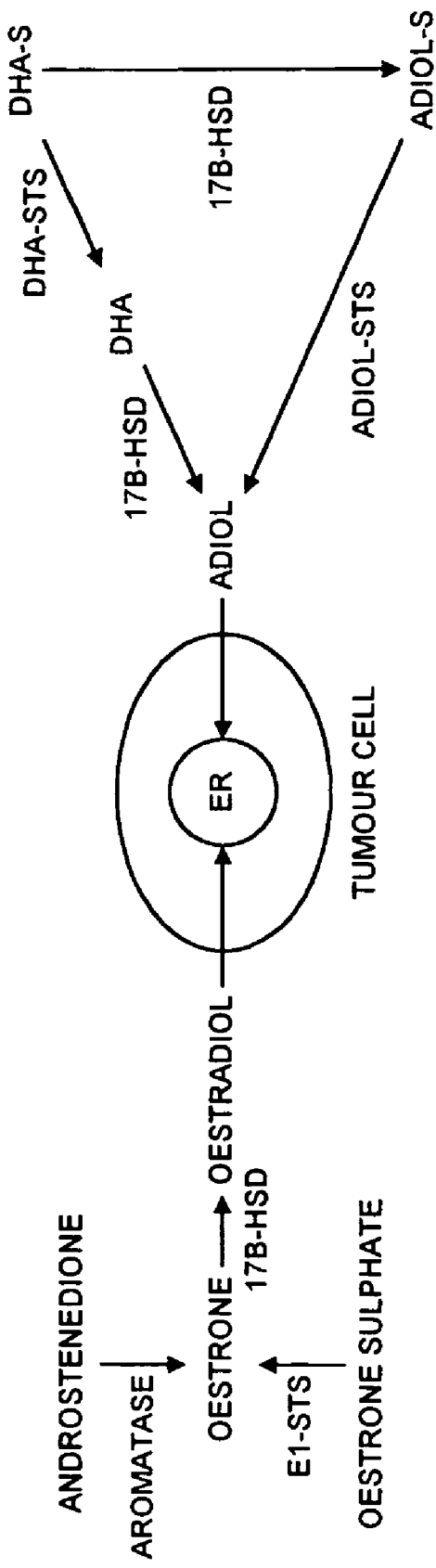

SULFAMIC ACID ESTER COMPOUNDS USEFUL IN THE INHIBITION OF STEROID SULPHATASE ACTIVITY AND AROMATASE ACTIVITY

REFERENCE TO RELATED APPLICATIONS

This application is a continuation-in-part of International Patent Application No. PCT/GB2005/001985 filed May 19, 2005 and published as WO 2005/115996 on Dec. 8, 2005, which claims priority from Great Britain patent application No. 0411562.2, filed May 24, 2004.

Each of the above referenced applications, and each document cited in this text ("application cited documents") and each document cited or referenced in each of the application cited documents, and any manufacturer's specifications or instructions for any products mentioned in this text and in any document incorporated into this text, are hereby incorporated herein by reference; and, technology in each of the documents incorporated herein by reference can be used in the practice of this invention.

It is noted that in this disclosure, terms such as "comprises", "comprised", "comprising", "contains", "containing" and the like can have the meaning attributed to them in U.S. Patent law; e.g., they can mean "includes", "included", "including" and the like. Terms such as "consisting essentially of" and "consists essentially of" have the meaning attributed to them in U.S. Patent law, e.g., they allow for the inclusion of additional ingredients or steps that do not detract from the novel or basic characteristics of the invention, i.e., they exclude additional unrecited ingredients or steps that detract from novel or basic characteristics of the invention, and they exclude ingredients or steps of the prior art, such as documents in the art that are cited herein or are incorporated by reference herein, especially as it is a goal of this document to define embodiments that are patentable, e.g., novel, non-obvious, inventive, over the prior art, e.g., over documents cited herein or incorporated by reference herein. And, the terms "consists of" and "consisting of" have the meaning ascribed to them in U.S. Patent law; namely, that these terms are closed ended.

FIELD OF INVENTION

The present invention relates to a compound.

In particular the present invention relates to a compound and to a pharmaceutical composition comprising the compound. The present invention also relates to the use of the compound or composition in therapy applications.

BACKGROUND TO THE INVENTION

Evidence suggests that oestrogens are the major mitogens involved in promoting the growth of tumours in endocrine-dependent tissues, such as the breast and endometrium. Although plasma oestrogen concentrations are similar in women with or without breast cancer, breast tumour oestrone and oestradiol levels are significantly higher than in normal breast tissue or blood. In situ synthesis of oestrogen is thought to make an important contribution to the high levels of oestrogens in tumours and therefore inhibitors, in particular specific inhibitors, of oestrogen biosynthesis are of potential value for the treatment of endocrine-dependent tumours.

Over the past two decades, there has been considerable interest in the development of inhibitors of the aromatase pathway—which converts the androgen precursor androstenedione to oestrone. However, there is now evidence that the oestrone sulphatase (E1-STS) pathway, i.e. the hydrolysis of oestrone sulphate to oestrone (E1S to E1), and aromatase (i.e. conversion of androstenedione to oestrone) account for the production of oestrogens in breast tumours.

FIGS. 1 and 2 are schematic diagrams showing some of the enzymes involved in the in situ synthesis of oestrone from oestrone sulphate, oestradiol and androstenedione.

In FIG. 2, which schematically shows the origin of oestrogenic steroids in postmenopausal women, "ER" denotes Oestrogen Receptor, "DHEA-S" denotes Dehydroepiandrosterone-Sulphate, "Adiol" denotes Androstenediol, "E1-STS" denotes Oestrone Sulphatase, "DHEA-STS" denotes DHEA-sulphatase, "Adiol-STS" denotes Adiol Sulphatase, and "17B-HSD" denotes Oestradiol 17B-hydroxysteroid dehydrogenase.

As can be seen, the main two enzymes that are involved in the peripheral synthesis of oestrogens are the aromatase enzyme and the enzyme oestrone sulphatase.

In short, the aromatase enzyme converts androstenedione, which is secreted in large amounts by the adrenal cortex, to oestrone. Recent reports have suggested that some flavones could inhibit aromatase activity.

Much of the oestrone so formed, however, is converted to oestrone sulphate (E1S) and there is now a considerable body of evidence showing that E1S in plasma and tissue acts as a reservoir for the formation of oestrone by the action of oestrone sulphatase.

In this regard, it is now believed that the oestrone sulphatase (E1-STS) pathway—i.e. the hydrolysis of oestrone sulphate to oestrone (E1S to E1) is a major source of oestrogen in breast tumours. This theory is supported by a modest reduction of plasma oestrogen concentration in postmenopausal women with breast cancer treated by aromatase inhibitors, such as aminoglutethimide and 4-hydroxyandrostenedione and also by the fact that plasma E1S concentration in these aromatase inhibitor-treated patients remains relatively high. The long half-life of E1S in blood (10-12 h) compared with the unconjugated oestrogens (20 min) and high levels of steroid sulphatase activity in liver and, normal and malignant breast tissues, also lend support to this theory.

Thus, oestrogen formation in malignant breast and endometrial tissues via the sulphatase pathway makes a major contribution to the high concentration of oestrogens which are present in these tumours. However, inhibition of both the aromatase and sulphatase pathways could offer considerable therapeutic benefit.

PCT/GB92/01587 teaches novel steroid sulphatase inhibitors and pharmaceutical compositions containing them for use in the treatment of oestrone dependent tumours, especially breast cancer. These steroid sulphatase inhibitors are sulphamate esters, such as N,N-dimethyl oestrone-3-sulphamate and, preferably, oestrone-3-sulphamate (otherwise known as "EMATE"). EMATE has the following structure:

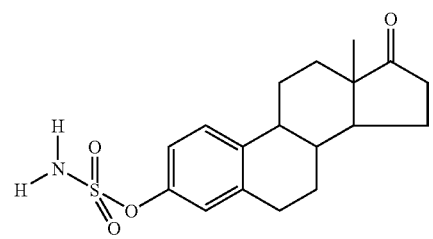

It is known that EMATE is a potent E1-STS inhibitor as it displays more than 99% inhibition of E1-STS activity in intact MCF-7 cells at 0.1 nM. EMATE also inhibits the E1-STS enzyme in a time- and concentration-dependent manner, indicating that it acts as an active site-directed inactivator. Although EMATE was originally designed for the inhibition of E1-STS, it also inhibits dehydroepiandrosterone sulphatase (DHEA-STS), which is an enzyme that is believed to have a pivotal role in regulating the biosynthesis of the oestrogenic steroid androstenediol. Also, there is now evidence to suggest that androstenediol may be of even greater importance as a promoter of breast tumour growth. EMATE is also active in vivo as almost complete inhibition of rat liver E1-STS (99%) and DHEA-STS (99%) activities resulted when it is administered either orally or subcutaneously. In addition, EMATE has been shown to have a memory enhancing effect in rats. Studies in mice have suggested an association between DHEA-STS activity and the regulation of part of the immune response. It is thought that this may also occur in humans. The bridging O-atom of the sulphamate moiety in EMATE is important for inhibitory activity. Thus, when the 3-O-atom is replaced by other heteroatoms as in oestrone-3-N-sulphamate and oestrone-3-S-sulphamate, these analogues are weaker non-time-dependent inactivators.

In addition to oestrone, the other major steroid with oestrogenic properties which is produced by postmenopausal women is androstenediol (see FIG. 2).

Androstenediol, although an androgen, can bind to the oestrogen receptor (ER) and can stimulate the growth of ER positive breast cancer cells and the growth of carcinogen-induced mammary tumours in the rat. Importantly, in postmenopausal women 90% of the androstenediol produced originates from the androgen dehydroepiandrosterone sulphate (DHEA-S) which is secreted in large amounts by the adrenal cortex. DHEA-S is converted to DHEA by DHEA sulphatase, which may be the same as, or different from, the enzyme, oestrone sulphatase, which is responsible for the hydrolysis of E1S.

During the last 10-15 years considerable research has also been carried out to develop potent aromatase inhibitors, some of which are now marketed. However, in three recent reports of postmenopausal women with breast cancer who received aromatase inhibitor therapy, plasma E1S concentrations remained between 400-1000 pg/ml.

In summation therefore in situ synthesis of oestrogen is thought to make an important contribution to the high levels of oestrogens in tumours and therefore specific inhibitors of oestrogen biosynthesis are of potential value for the treatment of endocrine-dependent tumours.

Moreover, even though oestrogen formation in malignant breast and endometrial tissues via the sulphatase pathway makes a major contribution to the high concentration of oestrogens, there are still other enzymatic pathways that contribute to in vivo synthesis of oestrogen.

Our earlier application WO03/045925 teaches compounds which may act as inhibitors of both aromatase and sulphatase. Many of the compounds of the disclosure are found to be extremely potent inhibitors of both of these enzymes. However, there is a desire to provide alternative compounds or improved compounds.

The present invention seeks to provide novel compounds suitable for the inhibition of steroid sulphatase activity and aromatase activity.

SUMMARY ASPECTS OF THE PRESENT INVENTION

The present invention is based on the surprising finding that certain polycyclic compounds could be used as effective steroid sulphatase inhibitors and/or aromatase inhibitors and/or as agents that can influence cell cycling and/or as agents that can influence apoptosis.

In one aspect, the present invention provides the selection of a certain subset of the compounds of WO03/045925. These compounds may act as effective steroid sulphatase inhibitors and/or aromatase inhibitors and/or as modulators of cell cycling and/or as modulators of apoptosis.

The polycyclic compounds comprise similar core structures to those of WO03/045925. However we have identified that by attaching the sulphamate group to its respective ring at a position meta to the attachment of the ring to the "central" nitrogen or carbon effective steroid sulphatase inhibitors and/or aromatase inhibitors and/or cell cycling modulators and/or apoptosis modulators may be provided.

The compounds of the present invention may comprise other substituents. These other substituents may, for example, further increase the activity of the compounds of the present invention and/or increase stability (ex vivo and/or in vivo).

BRIEF DESCRIPTION OF THE DRAWINGS

FIG. 2 is a schematic diagram showing some of the enzymes involved in the in situ synthesis of oestrone from oestrone sulphate, oestradiol and androstenedione.

DETAILED ASPECTS OF THE PRESENT INVENTION

Figure 1:
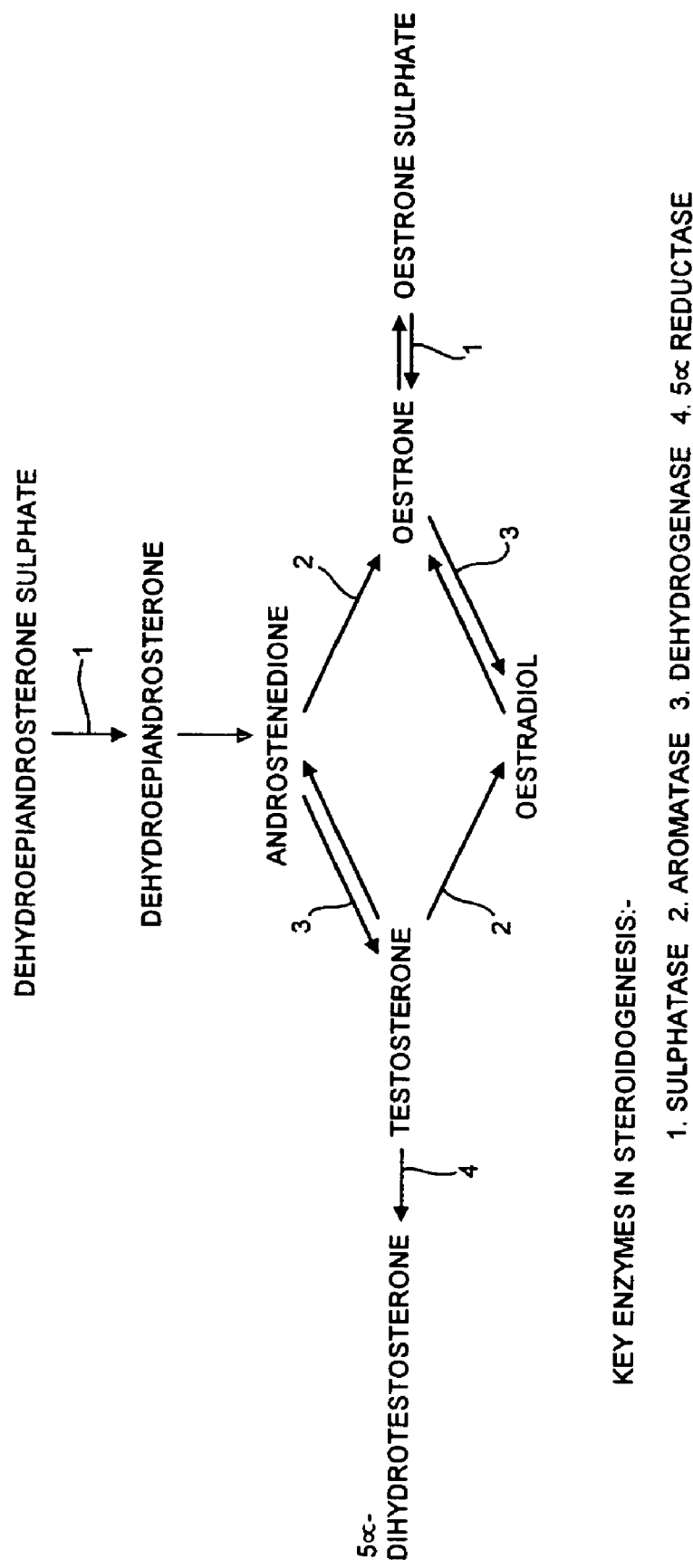
FIG. 1 is a schematic diagram showing some of the enzymes involved in the in situ synthesis of oestrone from oestrone sulphate, oestradiol and androstenedione.

According to one aspect of the present invention, there is provided a compound of Formula III or Formula IV

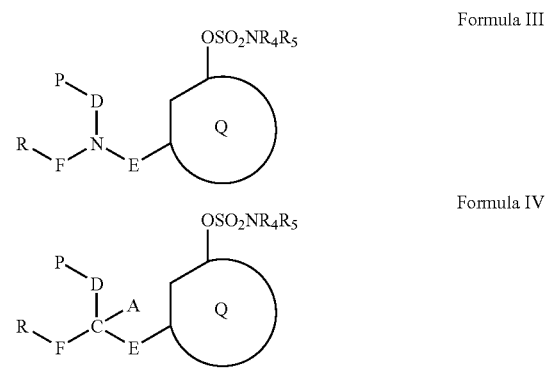

wherein
A is selected from H, OH, halogen and hydrocarbyl
D, E and F are each independently of each other an optional linker group;
P, Q and R are independently of each other a ring system;
wherein $R^4$ and $R^5$ are independently selected from H, alkyl, cycloalkyl, alkenyl, acyl and aryl, or combinations thereof, or together represent alkylene, wherein the or each alkyl or cycloalkyl or alkenyl or optionally contain one or more hetero atoms or groups.

According to one aspect of the present invention, there is provided a method comprising (a) performing a steroid sulphatase (STS) assay and/or aromatase assay with one or more candidate compounds defined herein; (b) determining whether one or more of said candidate compounds is/are capable of modulating STS activity and/or aromatase activity and/or cell cycling and/or cell growth and/or apoptosis; and (c) selecting one or more of said candidate compounds that is/are capable of modulating STS activity and/or aromatase activity and/or cell cycling and/or cell growth and/or apoptosis.

According to one aspect of the present invention, there is provided a method comprising (a) performing a steroid sulphatase assay and/or aromatase assay with one or more candidate compounds as defined herein; (b) determining whether one or more of said candidate compounds is/are capable of inhibiting STS and/or aromatase activity; and (c) selecting one or more of said candidate compounds that is/are capable of inhibiting STS activity and/or aromatase activity and/or cell cycling and/or cell growth and/or apoptosis.

In any one of the methods of the present invention, one or more additional steps may be present. For example, the method may also include the step of modifying the identified candidate compound (such as by chemical and/or enzymatic techniques) and the optional additional step of testing that modified compound for STS inhibition effects (which may be to see if the effect is greater or different) and/or aromatase inhibition effects (which may be to see if the effect is greater or different). By way of further example, the method may also include the step of determining the structure (such as by use of crystallographic techniques) of the identified candidate compound and then performing computer modelling studies—such as to further increase its STS and/or aromatase inhibitory action. Thus, the present invention also encompasses a computer having a dataset (such as the crystallographic co-ordinates) for said identified candidate compound. The present invention also encompasses that identified candidate compound when presented on a computer screen for the analysis thereof—such as enzyme and/or protein binding studies.

According to one aspect of the present invention, there is provided a compound identified by the method of the present invention.

According to one aspect of the present invention, there is provided a compound according to the present invention for use in medicine.

According to one aspect of the present invention, there is provided a pharmaceutical composition comprising the compound according to the present invention optionally admixed with a pharmaceutically acceptable carrier, diluent, excipient or adjuvant.

According to one aspect of the present invention, there is provided the use of a compound according to the present invention in the manufacture of a medicament for use in the therapy of a condition or disease associated with STS and/or aromatase and/or cell cycling and/or apoptosis and/or cell growth.

According to one aspect of the present invention, there is provided the use of a compound according to the present invention in the manufacture of a medicament for use in the therapy of a condition or disease associated with adverse STS levels and/or adverse aromatase levels and/or cell cycling and/or apoptosis and/or cell growth.

According to one aspect of the present invention, there is provided the use of a compound according to the present invention in the manufacture of a medicament for inhibiting STS activity and/or inhibiting aromatase activity.

According to one aspect of the present invention, there is provided the use of a compound according to the present invention in the manufacture of a medicament for inhibiting STS activity and inhibiting aromatase activity.

The present invention also encompasses the novel compounds of the present invention (such as those presented herein), as well as processes for making same (such as the processes presented herein) as well as novel intermediates (such as those presented herein) for use in those processes.

For ease of reference, these and further aspects of the present invention are now discussed under appropriate section headings. However, the teachings under each section are not necessarily limited to each particular section.

Some Advantages

One key advantage of the present invention is that the compounds of the present invention can act as STS inhibitors.

One key advantage of the present invention is that the compounds of the present invention can act as aromatase inhibitors.

One key advantage of the present invention is that the compounds of the present invention can act as STS inhibitors and aromatase inhibitors.

Another advantage of the compounds of the present invention is that they may be potent in vivo.

Some of the compounds of the present invention may be non-oestrogenic compounds. Here, the term "non-oestrogenic" means exhibiting no or substantially no oestrogenic activity. Here, by the term "non-oestrogenic" means exhibiting no or substantially no systemic oestrogenic activity, such as that determined by Protocol 4.

Another advantage is that some of the compounds may not be capable of being metabolised to compounds which display or induce hormonal activity.

Some of the compounds of the present invention are also advantageous in that they may be orally active.

Some of the compounds of the present invention may useful for the prevention and/or treatment of cancer, such as breast cancer, as well as (or in the alternative) non-malignant conditions, such as the prevention and/or treatment of inflammatory conditions—such as conditions associated with any one or more of: autoimmunity, including for example, rheumatoid arthritis, type I and II diabetes, systemic lupus erythematosus, multiple sclerosis, myasthenia gravis, thyroiditis, vasculitis, ulcerative colitis and Crohn's disease, skin disorders e.g. acne, psoriasis and contact dermatitis; graft versus host disease; eczema; asthma and organ rejection following transplantation. The compounds of the present invention are useful particularly when pharmaceuticals may need to be administered from an early age.

Thus, some of the compounds of the present invention are also believed to have therapeutic uses other than for the treatment of endocrine-dependent cancers, such as the treatment of autoimmune diseases.

The compounds of the present invention may also be useful as an inducer of apoptosis.

The compounds of the present invention may also be useful as a cell growth inhibitors.

Preferable Aspects

Preferably A is selected from H and hydrocarbyl. In one preferred aspect when A is a hydrocarbyl group it may be selected from $C_1$-$C_{10}$ hydrocarbyl,
$C_1$-$C_5$ hydrocarbyl
$C_1$-$C_3$ hydrocarbyl.
hydrocarbon groups
$C_1$-$C_{10}$ hydrocarbon
$C_1$-$C_5$ hydrocarbon
$C_1$-$C_3$ hydrocarbon.
alkyl groups
$C_1$-$C_{10}$ alkyl
$C_1$-$C_5$ alkyl
$C_1$-$C_3$ alkyl.

The hydrocarbyl/hydrocarbon/alkyl may be straight chain or branched and/or may be saturated or unsaturated.

The hydrocarbyl/hydrocarbon/alkyl may be straight or branched hydrocarbon groups containing at least one hetero atom in the group.

In a highly preferred aspect A is hydrogen.

Optional Linker—D, E and F

Independently of each other linker groups D, E and F may or may not be present. If present D, E or F may be selected from C=O and hydrocarbyl groups.

The term "hydrocarbyl group" as used herein means a group comprising at least C and H and may optionally comprise one or more other suitable substituents. Examples of such substituents may include halo, alkoxy, nitro, an alkyl group, a cyclic group etc. In addition to the possibility of the substituents being a cyclic group, a combination of substituents may form a cyclic group. If the hydrocarbyl group comprises more than one C then those carbons need not necessarily be linked to each other. For example, at least two of the carbons may be linked via a suitable element or group. Thus, the hydrocarbyl group may contain hetero atoms. Suitable hetero atoms will be apparent to those skilled in the art and include, for instance, sulphur, nitrogen and oxygen. A non-limiting example of a hydrocarbyl group is an acyl group.

A typical hydrocarbyl group is a hydrocarbon group. Here the term "hydrocarbon" means any one of an alkyl group, an alkenyl group, an alkynyl group, which groups may be linear, branched or cyclic, or an aryl group. The term hydrocarbon also includes those groups but wherein they have been optionally substituted. If the hydrocarbon is a branched structure having substituent(s) thereon, then the substitution may be on either the hydrocarbon backbone or on the branch; alternatively the substitutions may be on the hydrocarbon backbone and on the branch.

In one aspect when the compound is of Formula III, E is other than $CH_2$ and C=O Preferably D, E and F are independently selected from $C_1$-$C_{10}$ hydrocarbyl, $C_1$-$C_5$ hydrocarbyl or $C_1$-$C_3$ hydrocarbyl.

Preferably D, E and F are independently selected from hydrocarbon groups, preferably $C_1$-$C_{10}$ hydrocarbon, $C_1$-$C_5$ hydrocarbon or $C_1$-$C_3$ hydrocarbon.

Preferably D, E and F are independently selected from alkyl groups, $C_1$-$C_{10}$ alkyl, $C_1$-$C_5$ alkyl or $C_1$-$C_3$ alkyl.

The hydrocarbyl/hydrocarbon/alkyl of D, E and F may be straight chain or branched and/or may be saturated or unsaturated.

In one preferred aspect D, E and F are independently selected from straight or branched hydrocarbon groups containing at least one hetero atom in the group.

In a preferred aspect D, E and F are independently selected from hydrocarbon groups and a group of the formula

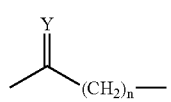

wherein n is 1 to 6 and Y=O, S or $CH_2$.

In a preferred aspect D, E and F are independently selected linear or branched hydrocarbon groups having a carbon chain of from 1 to 6 carbon atoms and a group of the formula

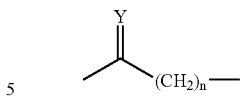

wherein n is 1 to 6 and Y=O, S or $CH_2$

In one preferred aspect only one of optional linker groups D, E and F is present. It will be understood that by only one it is meant that one of the linkers is present and the other optional linker group(s) is/are not present.

In one preferred aspect E (and preferably D and/or F) is selected from hydrocarbyl groups comprising at least two carbons or wherein the total number of carbons and hetero atoms is at least two.

In one preferred aspect E (and preferably D and/or F) is selected from hydrocarbyl groups containing at least one hetero atom in the group. Preferably the hetero atom is selected from sulphur, nitrogen and oxygen.

In one preferred aspect E (and preferably D and/or F) is selected from straight or branched hydrocarbon groups containing at least one hetero atom in the group. Preferably the hetero atom is selected from sulphur, nitrogen and oxygen.

In one preferred aspect E (and preferably D and/or F) is selected from hydrocarbon groups comprising at least 2 carbons and a group of the formula

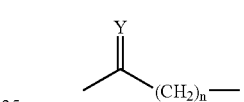

wherein n is 1 to 6 and Y=Oxygen, Sulphur or $CH_2$.

In one preferred aspect E (and preferably D and/or F) is selected from linear or branched hydrocarbon groups having a carbon chain of from 2 to 6 carbon atoms and a group of the formula

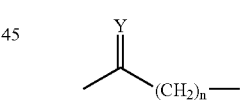

wherein n is 1 to 6 and Y=Oxygen, Sulphur or $CH_2$.

In one preferred aspect E (and preferably D and/or F) is selected from straight or branched alkyl groups, preferably $C_{1-10}$ alkyl, more preferably $C_{1-5}$ alkyl, containing at least one hetero atom in the group. Preferably the hetero atom is selected from sulphur, nitrogen and oxygen.

In one preferred aspect E (and preferably D and/or F) is selected from straight chain alkyl groups, preferably $C_{1-10}$ alkyl, more preferably $C_{1-5}$ alkyl, containing at least one hetero atom in the group. Preferably the hetero atom is selected from sulphur, nitrogen and oxygen.

When E (or D and/or F) contains a hetero atom, preferably the hetero atom is attached to the ring Q (or D or R in the case of D and F).

In a highly preferred aspect the compound of the present invention is of the formula

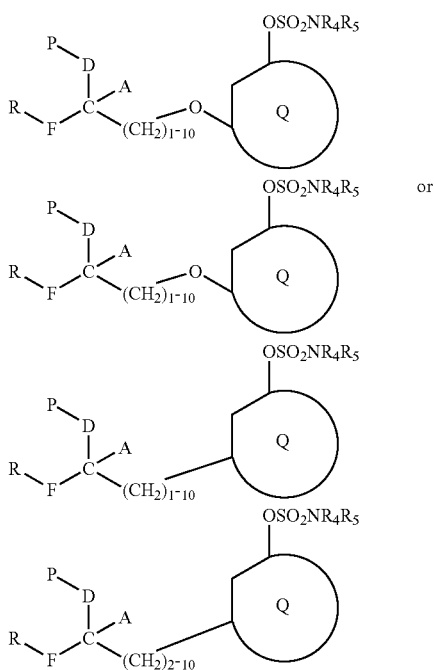

In a highly preferred aspect the compound of the present invention is of the formula

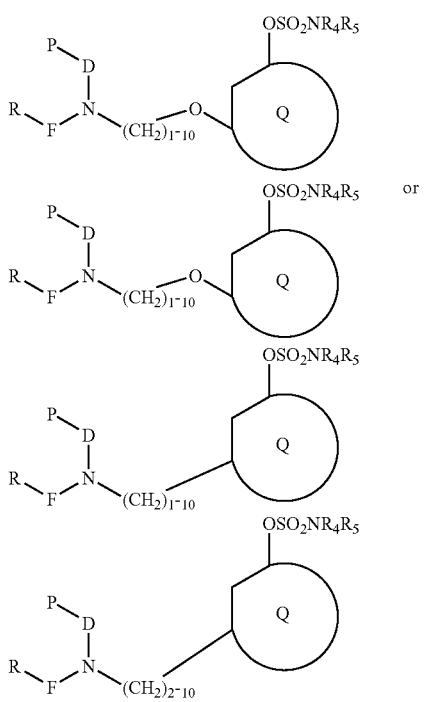

Rings—P, Q and R

The present compound comprises three ring systems each of which is attached directly or indirectly via linker D, E or F to the "central" N of Formula III or the "central" C of Formula IV. For each of P, Q and R the ring system need not be a cyclic structure. In this regard, the ring system may be a linear structure that may have the ability to conform to a ring like structure when in in vivo. However in preferred aspects each ring system is a cyclic structure.

In a preferred aspect, P, Q and R are independently selected from cyclic groups.

At least one of the cyclic groups P, Q and R may be a heterocyclic group (a heterocycle) or a non-heterocyclic group. Suitable hetero atoms of a heterocyclic group include N, S and O.

At least one of the cyclic groups P, Q and R may be ring systems comprising carbon and optionally one or more hetero atoms.

In a preferred aspect at least one of P, Q and R is, or P, Q and R are independently selected from a ring system comprising carbon and optionally one, two or three hetero atoms. Preferably at least one of P, Q and R is, or P, Q and R are independently selected from a ring system comprising carbon and one or more hetero atoms.

When hetero atoms are present in a ring system to provide a heterocyclic group, the hetero atoms may be present in any amount. In one preferred aspect at least one of P, Q and R is, or P, Q and R are independently selected from, a ring system comprising carbon and one or more hetero atoms selected from N, S and O.

When one of P, Q and R is a heterocyclic group the other of P, Q and R may or may not be heterocyclic groups. In a preferred aspect one of P, Q and R is a ring system comprising carbon and one or more hetero atoms and the other of P, Q and R are independently carbocyclic ring systems. It will be understood that by carbocyclic it is meant a ring system in which the ring contains only carbon atoms together with optional substituents on the ring. In this aspect preferably one of P, Q and R is a ring system comprising carbon and one or more hetero atoms selected from N, S and O and two of P, Q and R are independently carbocyclic ring systems.

In one aspect of the invention at least one of P, Q and R, or P, Q and R are independently selected a saturated ring structure or an unsaturated ring structure (such as an aryl group).

In one aspect of the invention at least one of P, Q and R, or P, Q and R are independently selected a saturated ring structure such a cycloalkyl group.

Preferably, at least one P, Q and R is an aryl ring.

In one aspect of the invention at least one of P, Q and R, or P, Q and R are independently selected from substituted or unsubstituted aromatic rings.

In one aspect of the invention at least one of P, Q and R is or comprises a substituted or unsubstituted aromatic ring.

In one aspect one of P, Q or R may be a polycyclic group, which need not be a fused polycycle. The term "polycyclic" includes fused and non-fused ring structures including combinations thereof. If the ring system of P, Q or R is polycyclic some or all of the ring components of the ring system may be fused together or joined via one or more suitable spacer groups.

The ring size of any of P, Q and R may be chosen by one skilled in the art to achieve compounds having desired activity. Typically P, Q and R are independently ring systems comprising from 3 to 10 members, such as ring systems comprising from 5, 6 or 7 members.

Heterocyclic ring systems for use in the present invention include imidazole, tetrazole, pyrazole, triazole, such as 1H-1,2,3-triazole, 1H-1,2,4-triazole, 4H-1,2,4-triazole; optionally substituted 5- or 6-membered heterocyclic group containing 1 to 3 hetero atoms each selected from N, O and S, optionally substituted aryl (monocyclic or polycyclic aromatic), pyridazine, pyrimidine, triazine such as 1,3,5 triazine, and optionally substituted bicyclic condensed heterocyclic group consisting of the above heterocyclic group condensed with benzene.

In a highly preferred aspect at least one of P, Q and R is, or P, Q and R are independently selected from triazole, in particular 1H-1,2,3-triazole, 1H-1,2,4-triazole, 4H-1,2,4-triazole In a highly preferred aspect at least one of P, Q and R is 4H-1,2,4-triazole.

In a highly preferred aspect at least one of P, Q and R is 1H-1,2,4-triazole.

In a highly preferred aspect at least one of P, Q and R is triazole, in particular 1H-1,2,3-triazole, 1H-1,2,4-triazole, 4H-1,2,4-triazole and the other of P, Q and R are substituted or unsubstituted benzyl rings.

In a highly preferred aspect at least one of P, Q and R is 4H-1,2,4-triazole and the other of P, Q and R are substituted or unsubstituted benzyl rings.

In the above aspects the triazole may be linked to X via a C in the triazole ring or a N in the triazole ring. In one aspect the triazole is linked to X via a C in the triazole ring.

In a preferred aspect P is a ring system comprising carbon and one or more hetero atoms and Q and R, if present, are independently carbocyclic ring systems.

In a preferred aspect P is a ring system comprising carbon and one or more hetero atoms selected from N, S and O and Q and R, if present, are independently carbocyclic ring systems.

In a preferred aspect Q and R, if present, are independently carbocyclic ring systems, and P is a ring system selected from imidazole, tetrazole, pyrazole, triazole, such as 1H-1,2,3-triazole, 1H-1,2,4-triazole, 4H-1,2,4-triazole; optionally substituted 5- or 6-membered heterocyclic group containing 1 to 3 hetero atoms each selected from N, O and S, optionally substituted aryl (monocyclic or polycyclic aromatic), pyridazine, pyrimidine, triazine such as 1,3,5 triazine, and optionally substituted bicyclic condensed heterocyclic group consisting of the above heterocyclic group condensed with benzene.

In a preferred aspect Q and R, if present, are independently carbocyclic ring systems, and P is a ring system selected from triazoles, in particular 1H-1,2,3-triazole, 1H-1,2,4-triazole, 4H-1,2,4-triazole.

In a preferred aspect Q and R, if present, are independently carbocyclic ring systems, and P is 4H-1,2,4-triazole.

In a preferred aspect Q and R, if present, are independently carbocyclic ring systems, and P is 1H-1,2,4-triazole.

In a preferred aspect P is a ring system comprising carbon and one or more hetero atoms and Q and R, if present, are independently optionally substituted benzyl rings.

In a preferred aspect P is a ring system comprising carbon and one or more hetero atoms selected from N, S and O and Q and R, if present, are independently optionally substituted benzyl rings.

In a preferred aspect Q and R, if present, are independently optionally substituted benzyl rings, and P is a ring system selected from imidazole, tetrazole, pyrazole, triazole, such as 1H-1,2,3-triazole, 1H-1,2,4-triazole, 4H-1,2,4-triazole; optionally substituted 5- or 6-membered heterocyclic group containing 1 to 3 hetero atoms each selected from N, O and S, optionally substituted aryl (monocyclic or polycyclic aromatic), pyridazine, pyrimidine, triazine such as 1,3,5triazine, and optionally substituted bicyclic condensed heterocyclic group consisting of the above heterocyclic group condensed with benzene.

In a preferred aspect Q and R, if present, are independently optionally substituted benzyl rings, and P is a ring system selected from triazoles, in particular 1H-1,2,3-triazole, 1H-1,2,4-triazole, 4H-1,2,4-triazole.

In a preferred aspect Q and R, if present, are independently optionally substituted benzyl rings, and P is 4H-1,2,4-triazole.

In a preferred aspect Q and R, if present, are independently optionally substituted benzyl rings, and P is 1H-1,2,4-triazole.

The ring systems P, Q and R may be substituted by one or more substituents. Preferred substituents (other than the required sulphamate group) include hydrocarbyl, oxyhydrocarbyl, halo and cyano (—C≡N) groups. The ring systems P, Q and R may also be substituted by one or more substituents selected from phosphonate groups, thiophosphonate groups, sulphonate groups and sulphonamide groups.

The ring system P may be substituted by one or more substituents. Preferred substituents (other than the required sulphamate group) include hydrocarbyl, oxyhydrocarbyl, halo and cyano (—C≡N) groups. The ring system P may also be substituted by one or more substituents selected from phosphonate groups, thiophosphonate groups, sulphonate groups and sulphonamide groups. In one preferred aspect P is unsubstituted.

The ring system R may be substituted by one or more substituents. Preferred substituents (other than the required sulphamate group) include hydrocarbyl, oxyhydrocarbyl, halo and cyano (—C≡N) groups. The ring system P may also be substituted by one or more substituents selected from phosphonate groups, thiophosphonate groups, sulphonate groups and sulphonamide groups.

In one preferred aspect R is substituted.

In one preferred aspect R, particularly when it is a carbocyclic group, is substituted with a cyano (—C≡N) group. In one preferred aspect R is substituted with a sulphamate group.

In one preferred aspect R is substituted with a group para to the attachment to the "central" carbon or nitrogen.

In one preferred aspect R is substituted with a group meta to the attachment to the "central" carbon or nitrogen.

In one preferred aspect R is substituted with a cyano group para to the attachment to the "central" carbon or nitrogen.

In one preferred aspect R is substituted with a sulphamate group meta to the attachment to the "central" carbon or nitrogen.

In addition to the essential sulphamate group, ring system Q may be substituted by one or more further substituents. Preferred substituents (other than the required sulphamate group) include hydrocarbyl, oxyhydrocarbyl, halo and cyano (—C≡N) groups. The ring system P may also be substituted by one or more substituents selected from phosphonate groups, thiophosphonate groups, sulphonate groups and sulphonamide groups.

In one preferred aspect Q is substituted with an oxyhydrocarbyl group. Preferably the oxyhydrocarbyl group is at a position ortho to the sulphamate group. Preferably the oxyhydrocarbyl group is at a position para to the attachment to the "central" carbon or nitrogen.

The term "oxyhydrocarbyl" group as used herein means a group comprising at least C, H and O and may optionally comprise one or more other suitable substituents. Examples of such substituents may include halo-, alkoxy-, nitro-, an alkyl group, a cyclic group etc. In addition to the possibility of the substituents being a cyclic group, a combination of substituents may form a cyclic group. If the oxyhydrocarbyl group comprises more than one C then those carbons need not necessarily be linked to each other. For example, at least two of the carbons may be linked via a suitable element or group. Thus, the oxyhydrocarbyl group may contain hetero atoms.

Suitable hetero atoms will be apparent to those skilled in the art and include, for instance, sulphur and nitrogen.

In one embodiment of the present invention, the oxyhydrocarbyl group is a oxyhydrocarbon group.

Here the term "oxyhydrocarbon" means any one of an alkoxy group, an oxyalkenyl group, an oxyalkynyl group, which groups may be linear, branched or cyclic, or an oxyaryl group. The term oxyhydrocarbon also includes those groups but wherein they have been optionally substituted. If the oxyhydrocarbon is a branched structure having substituent(s) thereon, then the substitution may be on either the hydrocarbon backbone or on the branch; alternatively the substitutions may be on the hydrocarbon backbone and on the branch.

Typically, the oxyhydrocarbyl group is of the formula $C_{1-6}O$ (such as a $C_{1-3}O$).

In one preferred aspect Q is substituted with a methoxy group.

Preferably Q is substituted with one or more halo atoms. Preferably the halo atoms are at a position ortho to the sulphamate group. Preferably the halo atom is at a position para to the attachment to the "central" carbon or nitrogen.

Further Preferred Compounds

In one preferred aspect the compound of the present invention is of the Formula IIIa

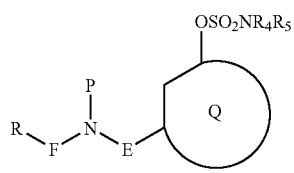

Formula IIIa wherein E and F are each independently of each other an optional linker group, P, Q and R are independently of each other a ring system and A is selected from H, OH, halogen and hydrocarbyl (preferably H)

In one preferred aspect the compound of the present invention is of the Formula IIIb

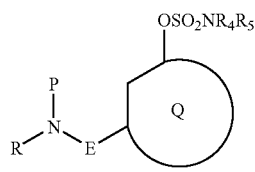

Formula IIIb wherein E is an optional linker group, P, Q and R are independently of each other a ring system and A is selected from H, OH, halogen and hydrocarbyl (preferably H).

In one preferred aspect the compound of the present invention is of the Formula IIIb

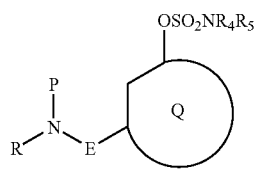

Formula IIIb wherein E is a linker group, P, Q and R are independently of each other a ring system and A is selected from H, OH, halogen and hydrocarbyl (preferably H).

In one preferred aspect the compound of the present invention is of the Formula IIIb

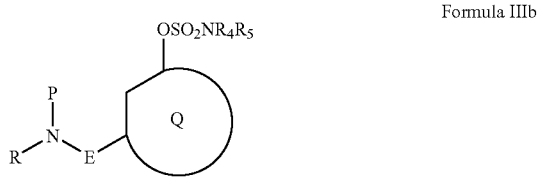

Formula IIIb wherein E is a straight chain or branched hydrocarbon group, preferably a $C_1$-$C_{10}$ hydrocarbon group containing at least two carbons or at least one hetero atom in the group; P, Q and R are independently of each other a ring system and A is selected from H, OH, halogen and hydrocarbyl (preferably H).

In one preferred aspect the compound of the present invention is of the Formula IVa

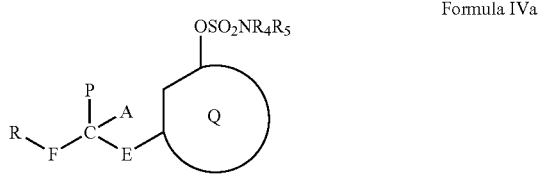

Formula IVa wherein E and F are each independently of each other an optional linker group, P, Q and R are independently of each other a ring system and A is selected from H, OH, halogen and hydrocarbyl (preferably H).

In one preferred aspect the compound of the present invention is of the Formula IVb

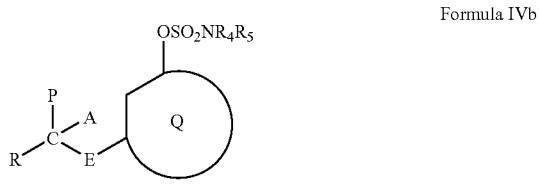

Formula IVb wherein E is an optional linker group, P, Q and R are independently of each other a ring system and A is selected from H, OH, halogen and hydrocarbyl (preferably H).

In one preferred aspect the compound of the present invention is of the Formula IVc

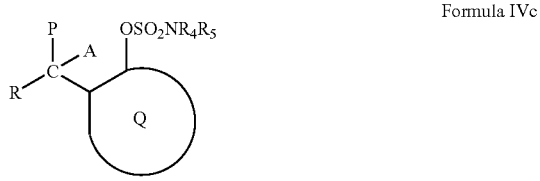

Formula IVc wherein P, Q and R are independently of each other a ring system; and at least Q comprises a sulphamate group and A is selected from H, OH, halogen and hydrocarbyl (preferably H).

In formulae IIIa, IIIb, IVa, IVb, IVc, preferably one of P, Q and R is a ring system comprising carbon and one or more hetero atoms and two of P, Q and R are independently selected from carbocyclic ring systems.

In formulae IIIa, IIIb, IVa, IVb, IVc, preferably one of P, Q and R is a ring system comprising carbon and one or more hetero atoms selected from Nitrogen, Sulphur and Oxygen and two of P, Q and R are independently selected from carbocyclic ring systems.

In formulae IIIa, IIIb, IVa, IVb, and IVc, preferably one of P, Q and R is 4H-1,2,4-triazole and two of P, Q and R are independently selected from substituted or unsubstituted benzyl rings.

In one preferred aspect the compound of the present invention is of the Formula V

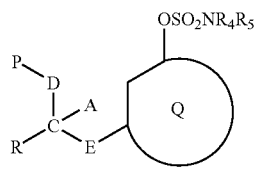

Formula V wherein D and E are each independently of each other an optional linker group, P, Q and R are independently of each other a ring system and A is selected from H, OH, halogen and hydrocarbyl (preferably H)

In one preferred aspect the compound of the present invention is of the Formula Va

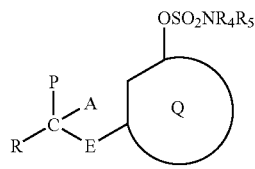

Formula Va wherein E is an optional linker group, P, Q and R are independently of each other a ring system, and A is selected from H, OH, halogen and hydrocarbyl (preferably H).

In one preferred aspect the compound of the present invention is of the Formula Vb

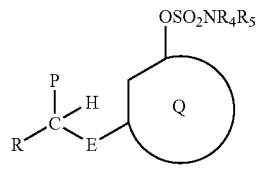

Formula Vb wherein E is an optional linker group, and wherein P, Q and R are independently of each other a ring system.

In one preferred aspect the compound of the present invention is of the Formula Vc

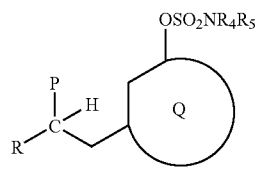

Formula Vc wherein P, Q and R are independently of each other a ring system.

In formulae V, Va, Vb and Vc, preferably one of P and Q is a ring system comprising carbon and one or more hetero atoms and the other of P and Q is a carbocyclic ring system.

In formulae V, Va, Vb and Vc, preferably one of P and Q is a ring system comprising carbon and one or more hetero atoms selected from Nitrogen, Sulphur and Oxygen and the other of P and Q is a carbocyclic ring system.

In formulae V, Va, Vb and Vc, preferably one of P and Q is 4H-1,2,4-triazole and the other of P and Q is a substituted or unsubstituted benzyl ring.

In one preferred aspect the compound of the present invention may be selected from compounds of one of the formulae below. In the formulae below each ring may be substituted or unsubstituted or may contain one or more additional bonds in the ring.

| Formula III Compounds | Formula IV Compounds |
|---|---|
| 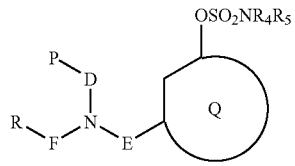 | 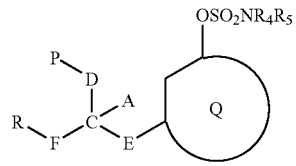 |
| 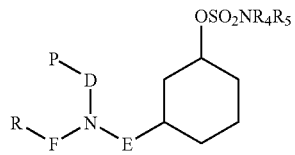 | 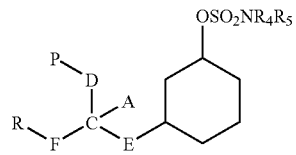 |

-continued

| Formula III Compounds | Formula IV Compounds |
|---|---|

In one preferred aspect the compound of the present invention may be selected from compounds of the formula

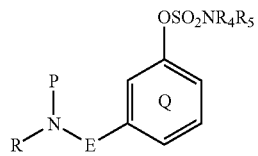

wherein P is ring system selected from imidazole, tetrazole, pyrazole, triazole, such as 1H-1,2,3-triazole, 1H-1,2,4-triazole, 4H-1,2,4-triazole wherein R is an optionally substituted phenyl group wherein Q is optionally substituted by a halo or alkoxy (such as a C1-6 alkoxy) group wherein E is selected from straight or branched alkyl groups, preferably $C_{1-10}$ alkyl, more preferably $C_{1-5}$ alkyl, containing at least one hetero atom in the group. Preferably the hetero atom is selected from sulphur, nitrogen and oxygen.

In one preferred aspect the compound of the present invention may be selected from compounds of the formula

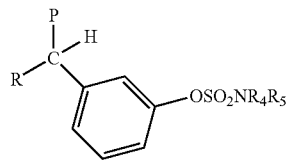

wherein P is ring system selected from imidazole, tetrazole, pyrazole, triazole, such as 1H-1,2,3-triazole, 1H-1,2,4-triazole, 4H-1,2,4-triazole wherein R is an optionally substituted phenyl group wherein Q is optionally substituted by a halo or alkoxy (such as a C1-6 alkoxy) group A highly preferred compound of the present invention is a compound selected from compounds of the formula

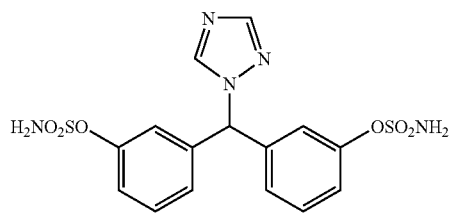

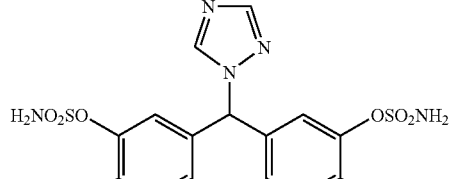

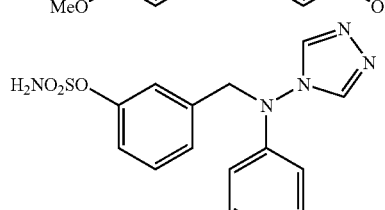

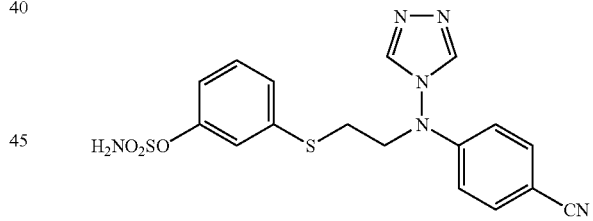

Sulphamate Group

At least ring Q one of the compound of the present invention comprises a sulphamate group.

For some compounds of the present invention, it is highly preferred that the compound comprises at least two or more sulphamate groups.

In one preferred aspect group R is substituted with a sulphamate. Preferably the sulphamate group is at a position meta to the attachment to the central carbon or nitrogen. Thus in one preferred aspect the present invention provides compounds of the formulae

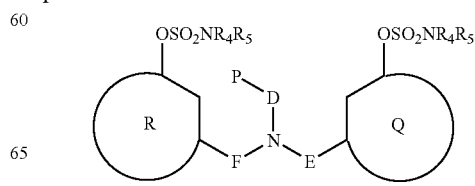

-continued

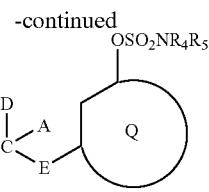

wherein $R^4$ and $R^5$ are each independently selected from H, alkyl, cycloalkyl, alkenyl, acyl and aryl, or combinations thereof, or together represent alkylene, wherein the or each alkyl or cycloalkyl or alkenyl or optionally contain one or more hetero atoms or groups.

For some compounds of the present invention, it is highly preferred that the compound comprises at least two sulphamate groups, wherein said sulphamate groups are not on the same ring.

For some applications, preferably the compounds have no, or a minimal, oestrogenic effect.

For some applications, preferably the compounds have an oestrogenic effect.

For some applications, preferably the compounds have a reversible action.

For some applications, preferably the compounds have an irreversible action.

In one embodiment, the compounds of the present invention are useful for the treatment of breast cancer.

The present invention also covers novel intermediates that are useful to prepare the compounds of the present invention and metabolites of the compounds of the present invention. For example, the present invention covers novel alcohol precursors for the compounds. By way of further example, the present invention covers bis protected precursors for the compounds. Examples of each of these precursors are presented herein. The present invention also encompasses a process comprising each or both of those precursors for the synthesis of the compounds of the present invention.

Steroid Sulphatase

Steroid sulphatase—which is sometimes referred to as steroid sulphatase or steryl sulphatase or "STS" for short—hydrolyses several sulphated steroids, such as oestrone sulphate, dehydroepiandrosterone sulphate and cholesterol sulphate. STS has been allocated the enzyme number EC 3.1.6.2.

STS has been cloned and expressed. For example see Stein et al (J. Biol. Chem. 264:13865-13872 (1989)) and Yen et al (Cell 49:443-454(1987)).

STS is an enzyme that has been implicated in a number of disease conditions.

By way of example, workers have found that a total deficiency in STS produces ichthyosis. According to some workers, STS deficiency is fairly prevalent in Japan. The same workers (Sakura et al, J Inherit Metab Dis 1997 November; 20(6):807-10) have also reported that allergic diseases—such as bronchial asthma, allergic rhinitis, or atopic dermatitis—may be associated with a steroid sulphatase deficiency.

In addition to disease states being brought on through a total lack of STS activity, an increased level of STS activity may also bring about disease conditions. By way of example, and as indicated above, there is strong evidence to support a role of STS in breast cancer growth and metastasis.

STS has also been implicated in other disease conditions. By way of example, Le Roy et al (Behav Genet March 1999; 29(2):131-6) have determined that there may be a genetic correlation between steroid sulphatase concentration and initiation of attack behaviour in mice. The authors conclude that sulphatation of steroids may be the prime mover of a complex network, including genes shown to be implicated in aggression by mutagenesis.

STS Inhibition

It is believed that some disease conditions associated with STS activity are due to conversion of a nonactive, sulphated oestrone to an active, nonsulphated oestrone. In disease conditions associated with STS activity, it would be desirable to inhibit STS activity.

Here, the term "inhibit" includes reduce and/or eliminate and/or mask and/or prevent the detrimental action of STS.

STS Inhibitor

In accordance with the present invention, the compound of the present invention is capable of acting as an STS inhibitor.

Here, the term "inhibitor" as used herein with respect to the compound of the present invention means a compound that can inhibit STS activity—such as reduce and/or eliminate and/or mask and/or prevent the detrimental action of STS. The STS inhibitor may act as an antagonist.

The ability of compounds to inhibit oestrone sulphatase activity can be assessed using either intact JEG3 choriocarcinoma cells or placental microsomes. In addition, an animal model may be used. Details on suitable Assay Protocols are presented in following sections. It is to be noted that other assays could be used to determine STS activity and thus STS inhibition. For example, reference may also be made to the teachings of WO-A-99/50453.

In one aspect, for some applications, the compound is further characterised by the feature that if the sulphamate group were to be substituted by a sulphate group to form a sulphate derivative, then the sulphate derivative would be hydrolysable by an enzyme having steroid sulphatase (E.C. 3.1.6.2) activity—i.e. when incubated with steroid sulphatase EC 3.1.6.2 at pH 7.4 and 37° C.

In one preferred embodiment, if the sulphamate group of the compound were to be replaced with a sulphate group to form a sulphate compound then that sulphate compound would be hydrolysable by an enzyme having steroid sulphatase (E.C. 3.1.6.2) activity and would yield a Km value of less than 200 mmolar, preferably less than 150 mmolar, preferably less than 100 mmolar, preferably less than 75 mmolar, preferably less than 50 mmolar, when incubated with steroid sulphatase EC 3.1.6.2 at pH 7.4 and 37° C.

For some applications, preferably the compound of the present invention has at least about a 100 fold selectivity to a desired target (e.g. STS and/or aromatase), preferably at least about a 150 fold selectivity to the desired target, preferably at least about a 200 fold selectivity to the desired target, preferably at least about a 250 fold selectivity to the desired target, preferably at least about a 300 fold selectivity to the desired target, preferably at least about a 350 fold selectivity to the desired target.

It is to be noted that the compound of the present invention may have other beneficial properties in addition to or in the alternative to its ability to inhibit STS and/or aromatase activity.

Sulphamate Group

The term "sulphamate" as used herein includes an ester of sulphamic acid, or an ester of an N-substituted derivative of sulphamic acid, or a salt thereof.

If $R^3$ is a sulphamate group then the compound of the present invention is referred to as a sulphamate compound.

Typically, the sulphamate group has the formula:

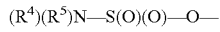

wherein preferably $R^4$ and $R^5$ are independently selected from H, alkyl, cycloalkyl, alkenyl, acyl and aryl, or combinations thereof, or together represent alkylene, wherein the or each alkyl or cycloalkyl or alkenyl or optionally contain one or more hetero atoms or groups.

When substituted, the N-substituted compounds of this invention may contain one or two N-alkyl, N-alkenyl, N-cycloalkyl or N-aryl substituents, preferably containing or each containing a maximum of 10 carbon atoms. When $R^4$ and/or $R^5$ is alkyl, the preferred values are those where $R^4$ and $R^5$ are each independently selected from lower alkyl groups containing from 1 to 6 carbon atoms, that is to say methyl, ethyl, propyl etc. $R^4$ and $R^5$ may both be methyl. When $R^4$ and/or $R^5$ is aryl, typical values are phenyl and tolyl ($PhCH_3$; o). Where $R^4$ and $R^5$ represent cycloalkyl, typical values are cyclopropyl, cyclopentyl, cyclohexyl etc. When joined together $R^4$ and $R^5$ typically represent an alkylene group providing a chain of 4 to 6 carbon atoms, optionally interrupted by one or more hetero atoms or groups, e.g. to provide a 5 membered heterocycle, e.g. morpholino, pyrrolidino or piperidino.

Within the values alkyl, cycloalkyl, alkenyl, acyl and aryl substituted groups are included containing as substituents therein one or more groups which do not interfere with the sulphatase inhibitory activity of the compound in question. Exemplary non-interfering substituents include hydroxy, amino, halo, alkoxy, alkyl and aryl.

In some embodiments, the sulphamate group may form a ring structure by being fused to (or associated with) one or more atoms in or on group X.

In some embodiments, there may be more than one sulphamate group. By way of example, there may be two sulphamates (i.e. bis-sulphamate compounds).

In some preferred embodiments, at least one of $R^4$ and $R^5$ is H.

In some further preferred embodiments, each of $R^4$ and $R^5$ is H.

Other Substituents

The compound of the present invention may have substituents other than those of formula I. By way of example, these other substituents may be one or more of: one or more sulphamate group(s), one or more phosphonate group(s), one or more thiophosphonate group(s), one or more sulphonate group(s), one or more sulphonamide group(s), one or more halo groups, one or more O groups, one or more hydroxy groups, one or more amino groups, one or more sulphur containing group(s), one or more hydrocarbyl group(s)—such as an oxyhydrocarbyl group.

Assay for Determining STS Activity Using Cancer Cells

Protocol 1

Inhibition of Steroid Sulphatase Activity in JEG3 Cells

Steroid sulphatase activity is measured in vitro using intact JEG3 choriocarcinoma cells. This cell line may be used to study the control of human breast cancer cell growth. It possesses significant steroid sulphatase activity (Boivin et al., J. Med. Chem., 2000, 43: 4465-4478) and is available in from the American Type Culture Collection (ATCC).

Cells are maintained in Minimal Essential Medium (MEM) (Flow Laboratories, Irvine, Scotland) containing 20 mM HEPES, 5% foetal bovine serum, 2 mM glutamine, non-essential amino acids and 0.075% sodium bicarbonate. Up to 30 replicate 25 cm2 tissue culture flasks are seeded with approximately $1 \times 10^5$ cells/flask using the above medium. Cells are grown to 80% confluency and the medium is changed every third day.

Intact monolayers of JEG3 cells in triplicate 25 cm² tissue culture flasks are washed with Earle's Balanced Salt Solution (EBSS from ICN Flow, High Wycombe, U.K.) and incubated for 3-4 hours at 37° C. with 5 pmol ($7 \times 10^5$ dpm) [6,7-3H] oestrone-3-sulphate (specific activity 60 Ci/mmol from New England Nuclear, Boston, Mass., U.S.A.) in serum-free MEM (2.5 ml) together with oestrone-3-sulphamate (11 concentrations: 0; 1 fM; 0.01 pM; 0.1 pM; 1 pM; 0.01 nM; 0.1 nM; 1 nM; 0.01 mM; 0.1 mM; 1 mM). After incubation each flask is cooled and the medium (1 ml) is pipetted into separate tubes containing [14C]oestrone ($7 \times 103$ dpm) (specific activity 97 Ci/mmol from Amersham International Radiochemical Centre, Amersham, U.K.). The mixture is shaken thoroughly for 30 seconds with toluene (5 ml). Experiments have shown that >90% [14C] oestrone and <0.1% [3H]oestrone-3-sulphate is removed from the aqueous phase by this treatment. A portion (2 ml) of the organic phase is removed, evaporated and the 3H and 14C content of the residue determined by scintillation spectrometry. The mass of oestrone-3-sulphate hydrolysed was calculated from the 3H counts obtained (corrected for the volumes of the medium and organic phase used, and for recovery of [14C] oestrone added) and the specific activity of the substrate. Each batch of experiments includes incubations of microsomes prepared from a sulphatase-positive human placenta (positive control) and flasks without cells (to assess apparent non-enzymatic hydrolysis of the substrate). The number of cell nuclei per flask is determined using a Coulter Counter after treating the cell monolayers with Zaponin. One flask in each batch is used to assess cell membrane status and viability using the Trypan Blue exclusion method (Phillips, H. J. (1973) In: Tissue culture and applications, [eds: Kruse, D. F. & Patterson, M. K.]; pp. 406-408; Academic Press, New York).

Results for steroid sulphatase activity are expressed as the mean±1 S.D. of the total product (oestrone+oestradiol) formed during the incubation period (3-4 hours) calculated for 106 cells and, for values showing statistical significance, as a percentage reduction (inhibition) over incubations containing no oestrone-3-sulphamate. Unpaired Student's t-test was used to test the statistical significance of results.

Assay for Determining STS Activity Using Placental Microsomes

Protocol 2

Inhibition of Steroid Sulphatase Activity in Placental Microsomes

Sulphatase-positive human placenta from normal term pregnancies are thoroughly minced with scissors and washed once with cold phosphate buffer (pH 7.4, 50 mM) then re-suspended in cold phosphate buffer (5 ml/g tissue). Homogenisation is accomplished with an Ultra-Turrax homogeniser, using three 10 second bursts separated by 2 minute cooling periods in ice. Nuclei and cell debris are removed by centrifuging (4° C.) at 2000 g for 30 minutes and portions (2 ml) of the supernatant are stored at 20° C. The protein concentration of the supernatants is determined by the method of Bradford (Anal. Biochem., 72, 248-254 (1976)).

Incubations (1 ml) are carried out using a protein concentration of 100 mg/ml, substrate concentration of 20 mM [6,7-3H]oestrone-3-sulphate (specific activity 60 Ci/mmol from New England Nuclear, Boston, Mass., U.S.A.) and an incubation time of 20 minutes at 37° C. If necessary eight concentrations of compounds are employed: 0 (i.e. control); 0.05 mM; 0.1 mM; 0.2 mM; 0.4 mM; 0.6 mM; 0.8 mM; 10 mM. After incubation each sample is cooled and the medium (1 ml)

was pipetted into separate tubes containing [14C]oestrone (7×10³ dpm) (specific activity 97 Ci/mmol from Amersham International Radiochemical Centre, Amersham, U.K.). The mixture is shaken thoroughly for 30 seconds with toluene (5 ml). Experiments have shown that >90% [14C]oestrone and <0.1% [3H]oestrone-3-sulphate is removed from the aqueous phase by this treatment. A portion (2 ml) of the organic phase was removed, evaporated and the 3H and 14C content of the residue determined by scintillation spectrometry. The mass of oestrone-3-sulphate hydrolysed is calculated from the 3H counts obtained (corrected for the volumes of the medium and organic phase used, and for recovery of [14C]oestrone added) and the specific activity of the substrate.

Animal Assay Model for Determining STS Activity

Protocol 3

Inhibition of Oestrone Sulphatase Activity In Vivo

The compounds of the present invention may be studied using an animal model, in particular in ovariectomised rats. In this model compounds which are oestrogenic stimulate uterine growth.

The compound (0.1 mg/Kg/day for five days) is administered orally to rats with another group of animals receiving vehicle only (propylene glycol). At the end of the study samples of liver tissue were obtained and oestrone sulphatase activity assayed using 3H oestrone sulphate as the substrate as previously described (see PCT/GB95/02638).

Animal Assay Model for Determining Oestrogenic Activity

Protocol 4

The compounds of the present invention may be studied using an animal model, in particular in ovariectomised rats. In this model, compounds which are oestrogenic stimulate uterine growth.

The compound (0.1 mg/Kg/day for five days) was administered orally to rats with another group of animals receiving vehicle only (propylene glycol). At the end of the study uteri were obtained and weighed with the results being expressed as uterine weight/whole body weight ×100.

Compounds having no significant effect on uterine growth are not oestrogenic.

Biotechnological Assays for Determining STS Activity

Protocol 5

The ability of compounds to inhibit oestrone sulphatase activity can also be assessed using amino acid sequences or nucleotide sequences encoding STS, or active fragments, derivatives, homologues or variants thereof in, for example, high-through put screens. Such assays and methods for their pratice are taught in WO 03/045925 which is incorporated herein by reference.

In one preferred aspect, the present invention relates to a method of identifying agents that selectively modulate STS, which compounds have the formula (I).

Assay for Determining Aromatase Activity Using JEG3 Cells

Protocol 6

Aromatase activity is measured in JEG3 choriocarcinoma cells, obtained from the ATCC. This cell line possesses significant aromatase activity and is widely used to study the control of human aromatase activity (Bhatnager et al., J. Steroid Biochem. Molec. Biol. 2001, 76: 199-202). Cells are maintained in Minimal Essential Medium (MEM, Flow Laboratories, Irvine, Scotland) containing 20 mM HEPES, 10% foetal bovine serum, 2 mM glutamine, non-essential amino acids and 0.075% sodium bicarbonate. Intact monolayers of JEG3 cells ($2.5 \times 10^6$ cells) in triplicate 25 cm² tissue culture flasks are washed with Earle's Balanced salt solution (EBSS, from ICN Flow, High Wycombe, UK) and incubated with [$1\beta$-$^3$H] androstenedione (2-5 nM, 26 Ci/mmol, New England Nuclear, Boston, Mass., USA) for 30 min with inhibitors over the range of 10 pm-10 μM. During the aromatase reaction, $^3$H$_2$O is liberated which can he quantified using a liquid scintillation spectrometer (Beckman-Coulter, High Wycombe, Bucks. UK). This $^3$H$_2$O-release method has been widely used to measure aromatase activity (Newton et al., J. Steroid Biochem. 1986, 24: 1033-1039). The number of cell nuclei per flask is determined using a Coulter Counter after treating the cell monolayers with Z aponin.

Results for aromatase activity are expressed as the mean±1 S.D. of the product formed during the incubation period (30 min) calculated for $10^6$ cells and, for values showing a statistical significance, as a percentage reduction (inhibition) over incubations containing no aromatase inhibitor. Unpaired Student's t test was used to test the statistical significance of results. $IC_{50}$ values were calculated as the concentration of inhibitor required to obtain a 50% inhibition of aromatase activity.

Animal Assays for Determining Aromatase Activity

Protocol 7

(i) Inhibition of PMSG-Induced Oestrogen Synthesis

The ability of compounds to inhibit aromatase activity in vivo was tested using a pregnant mare serum gonadotrophin (PMSG)-induced oestrogen synthesis assay. For this, female rats (250 g) were injected with PMSG (200 IU, s.c.). After 72 h rats were administered vehicle (propylene glycol) or various doses of test compounds orally. At 2 h after dosing blood samples were obtained by cardiac puncture (under anaesthesia). Plasma oestradiol levels were measured in control groups and groups receiving drugs. The efficacy of aromatase inhibition was determined by measurement of plasma oestradiol concentrations by radioimmunoassay. This method has been widely used to determine the effectiveness of aromatase inhibitors in vivo (Wouters et al., J. Steroid Biochem., 1989, 32:781-788).

(ii) Inhibition of Androstenedione Stimulated Uterine Growth in Ovariectomised Rats Female rats (250 g) were ovariectomised and used to determine the effectiveness of aromatase inhibition on androstenedione stimulated uterine growth. Administration of androstenedione (30 mg/kg/d) for a 2-week period results in a significant increase in uterine growth in ovariectomised animals. This increase in uterine growth is stimulated by oestrogen which is derived from the administered androstenedione as a result of the action of the aromatase enzyme. By coadministration of compounds with androstenedione the extent of aromatase inhibition can be determined by measurements of uterine weights in treated and untreated animals.

Therapy

The compounds of the present invention may be used as therapeutic agents—i.e. in therapy applications.

The term "therapy" includes curative effects, alleviation effects, and prophylactic effects.

The therapy may be on humans or animals, preferably female animals.

Pharmaceutical Compositions

In one aspect, the present invention provides a pharmaceutical composition, which comprises a compound according to the present invention and optionally a pharmaceutically acceptable carrier, diluent or excipient (including combinations thereof).

The pharmaceutical compositions may be for human or animal usage in human and veterinary medicine and will typically comprise any one or more of a pharmaceutically acceptable diluent, carrier, or excipient. Acceptable carriers or diluents for therapeutic use are well known in the pharmaceutical art, and are described, for example, in Remington's Pharmaceutical Sciences, Mack Publishing Co. (A. R. Gennaro edit. 1985). The choice of pharmaceutical carrier, excipient or diluent can be selected with regard to the intended route of administration and standard pharmaceutical practice. The pharmaceutical compositions may comprise as—or in addition to—the carrier, excipient or diluent any suitable binder(s), lubricant(s), suspending agent(s), coating agent(s), solubilising agent(s).

Preservatives, stabilisers, dyes and even flavouring agents may be provided in the pharmaceutical composition. Examples of preservatives include sodium benzoate, sorbic acid and esters of p-hydroxybenzoic acid. Antioxidants and suspending agents may be also used.

There may be different composition/formulation requirements dependent on the different delivery systems. By way of example, the pharmaceutical composition of the present invention may be formulated to be delivered using a mini-pump or by a mucosal route, for example, as a nasal spray or aerosol for inhalation or ingestable solution, or parenterally in which the composition is formulated by an injectable form, for delivery, by, for example, an intravenous, intramuscular or subcutaneous route. Alternatively, the formulation may be designed to be delivered by both routes.

Where the agent is to be delivered mucosally through the gastrointestinal mucosa, it should be able to remain stable during transit though the gastrointestinal tract; for example, it should be resistant to proteolytic degradation, stable at acid pH and resistant to the detergent effects of bile.

Where appropriate, the pharmaceutical compositions can be administered by inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or they can be injected parenterally, for example intravenously, intramuscularly or subcutaneously. For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner.

Combination Pharmaceutical

The compound of the present invention may be used in combination with one or more other active agents, such as one or more other pharmaceutically active agents.

By way of example, the compounds of the present invention may be used in combination with other STS inhibitors and/or other inhibitors such as an aromatase inhibitor (such as for example, 4-hydroxyandrostenedione (4-OHA)) and/or steroids—such as the naturally occurring neurosteroids dehydroepiandrosterone sulfate (DHEAS) and pregnenolone sulfate (PS) and/or other structurally similar organic compounds. Examples of other STS inhibitors may be found in the above references. By way of example, STS inhibitors for use in the present invention include EMATE, and either or both of the 2-ethyl and 2-methoxy 17-deoxy compounds that are analogous to compound 5 presented herein.

In addition, or in the alternative, the compound of the present invention may be used in combination with a biological response modifier.

The term biological response modifier ("BRM") includes cytokines, immune modulators, growth factors, haematopoiesis regulating factors, colony stimulating factors, chemotactic, haemolytic and thrombolytic factors, cell surface receptors, ligands, leukocyte adhesion molecules, monoclonal antibodies, preventative and therapeutic vaccines, hormones, extracellular matrix components, fibronectin, etc. For some applications, preferably, the biological response modifier is a cytokine. Examples of cytokines include: interleukins (IL)—such as IL-1, IL-2, IL-3, IL-4, IL-5, IL-6, IL-7, IL-8, IL-9, IL-10, IL-11, IL-12, IL-19; Tumour Necrosis Factor (TNF)—such as TNF-$\alpha$; Interferon alpha, beta and gamma; TGF-$\beta$. For some applications, preferably the cytokine is tumour necrosis factor (TNF). For some applications, the TNF may be any type of TNF—such as TNF-$\alpha$, TNF-$\beta$, including derivatives or mixtures thereof. More preferably the cytokine is TNF-$\alpha$. Teachings on TNF may be found in the art—such as WO-A-98/08870 and WO-A-98/13348.

Administration

Typically, a physician will determine the actual dosage which will be most suitable for an individual subject and it will vary with the age, weight and response of the particular patient. The dosages below are exemplary of the average case. There can, of course, be individual instances where higher or lower dosage ranges are merited.

The compositions of the present invention may be administered by direct injection. The composition may be formulated for parenteral, mucosal, intramuscular, intravenous, subcutaneous, intraocular or transdermal administration. Depending upon the need, the agent may be administered at a dose of from 0.01 to 30 mg/kg body weight, such as from 0.1 to 10 mg/kg, more preferably from 0.1 to 1 mg/kg body weight.

By way of further example, the agents of the present invention may be administered in accordance with a regimen of 1 to 4 times per day, preferably once or twice per day. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Aside from the typical modes of delivery—indicated above—the term "administered" also includes delivery by techniques such as lipid mediated transfection, liposomes, immunoliposomes, lipofectin, cationic facial amphiphiles (CFAs) and combinations thereof. The routes for such delivery mechanisms include but are not limited to mucosal, nasal, oral, parenteral, gastrointestinal, topical, or sublingual routes.

The term "administered" includes but is not limited to delivery by a mucosal route, for example, as a nasal spray or aerosol for inhalation or as an ingestable solution; a parenteral route where delivery is by an injectable form, such as, for example, an intravenous, intramuscular or subcutaneous route.

Thus, for pharmaceutical administration, the STS inhibitors of the present invention can be formulated in any suitable manner utilising conventional pharmaceutical formulating techniques and pharmaceutical carriers, adjuvants, excipients, diluents etc. and usually for parenteral administration. Approximate effective dose rates may be in the range from 1 to 1000 mg/day, such as from 10 to 900 mg/day or even from 100 to 800 mg/day depending on the individual activities of the compounds in question and for a patient of average (70 Kg) bodyweight. More usual dosage rates for the preferred and more active compounds will be in the range 200 to 800 mg/day, more preferably, 200 to 500 mg/day, most preferably from 200 to 250 mg/day. They may be given in single dose regimes, split dose regimes and/or in multiple dose regimes lasting over several days. For oral administration they may be formulated in tablets, capsules, solution or suspension containing from 100 to 500 mg of compound per unit dose. Alternatively and preferably the compounds will be formulated for parenteral administration in a suitable parenterally administrable carrier and providing single daily dosage rates in the range 200 to 800 mg, preferably 200 to 500, more preferably 200 to 250 mg. Such effective daily doses will, however, vary depending on inherent activity of the active ingredient and on the bodyweight of the patient, such variations being within the skill and judgement of the physician.

Cell Cycling

The compounds of the present invention may be useful in the method of treatment of a cell cycling disorder.

As discussed in "Molecular Cell Biology" 3rd Ed. Lodish et al. pages 177-181 different eukaryotic cells can grow and divide at quite different rates. Yeast cells, for example, can divide every 120 min., and the first divisions of fertilised eggs in the embryonic cells of sea urchins and insects take only 1530 min. because one large pre-existing cell is subdivided. However, most growing plant and animal cells take 10-20 hours to double in number, and some duplicate at a much slower rate. Many cells in adults, such as nerve cells and striated muscle cells, do not divide at all; others, like the fibroblasts that assist in healing wounds, grow on demand but are otherwise quiescent.

Still, every eukaryotic cell that divides must be ready to donate equal genetic material to two daughter cells. DNA synthesis in eukaryotes does not occur throughout the cell division cycle but is restricted to a part of it before cell division.

The relationship between eukaryotic DNA synthesis and cell division has been thoroughly analysed in cultures of mammalian cells that were all capable of growth and division. In contrast to bacteria, it was found, eukaryotic cells spend only a part of their time in DNA synthesis, and it is completed hours before cell division (mitosis). Thus a gap of time occurs after DNA synthesis and before cell division; another gap was found to occur after division and before the next round of DNA synthesis. This analysis led to the conclusion that the eukaryotic cell cycle consists of an M (mitotic) phase, a $G_1$ phase (the first gap), the S (DNA synthesis) phase, a $G_2$ phase (the second gap), and back to M. The phases between mitoses ($G_1$, S, and $G_2$) are known collectively as the interphase.

Many nondividing cells in tissues (for example, all quiescent fibroblasts) suspend the cycle after mitosis and just prior to DNA synthesis; such "resting" cells are said to have exited from the cell cycle and to be in the $G_0$ state.

It is possible to identify cells when they are in one of the three interphase stages of the cell cycle, by using a fluorescence-activated cell sorter (FACS) to measure their relative DNA content: a cell that is in $G_1$ (before DNA synthesis) has a defined amount x of DNA; during S (DNA replication), it has between x and 2x; and when in $G_2$ (or M), it has 2x of DNA.

The stages of mitosis and cytokinesis in an animal cell are as follows (a) Interphase. The $G_2$ stage of interphase immediately precedes the beginning of mitosis. Chromosomal DNA has been replicated and bound to protein during the S phase, but chromosomes are not yet seen as distinct structures. The nucleolus is the only nuclear substructure that is visible under light microscope. In a diploid cell before DNA replication there are two morphologic chromosomes of each type, and the cell is said to be 2n. In $G_2$, after DNA replication, the cell is 4n. There are four copies of each chromosomal DNA. Since the sister chromosomes have not yet separated from each other, they are called sister chromatids.

b) Early prophase. Centrioles, each with a newly formed daughter centriole, begin moving toward opposite poles of the cell; the chromosomes can be seen as long threads. The nuclear membrane begins to disaggregate into small vesicles.

(c) Middle and late prophase. Chromosome condensation is completed; each visible chromosome structure is composed of two chromatids held together at their centromeres. Each chromatid contains one of the two newly replicated daughter DNA molecules. The microtubular spindle begins to radiate from the regions just adjacent to the centrioles, which are moving closer to their poles. Some spindle fibres reach from pole to pole; most go to chromatids and attach at kinetochores.

(d) Metaphase. The chromosomes move toward the equator of the cell, where they become aligned in the equatorial plane. The sister chromatids have not yet separated.

(e) Anaphase. The two sister chromatids separate into independent chromosomes. Each contains a centromere that is linked by a spindle fibre to one pole, to which it moves. Thus one copy of each chromosome is donated to each daughter cell. Simultaneously, the cell elongates, as do the pole-to-pole spindles. Cytokinesis begins as the cleavage furrow starts to form.

(f) Telophase. New membranes form around the daughter nuclei; the chromosomes uncoil and become less distinct, the nucleolus becomes visible again, and the nuclear membrane forms around each daughter nucleus. Cytokinesis is nearly complete, and the spindle disappears as the microtubules and other fibres depolymerise. Throughout mitosis the "daughter" centriole at each pole grows until it is full-length. At telophase the duplication of each of the original centrioles is completed, and new daughter centrioles will be generated during the next interphase.

(g) Interphase. Upon the completion of cytokinesis, the cell enters the $G_1$ phase of the cell cycle and proceeds again around the cycle.

It will be appreciated that cell cycling is an extremely important cell process. Deviations from normal cell cycling can result in a number of medical disorders. Increased and/or unrestricted cell cycling may result in cancer. Reduced cell cycling may result in degenerative conditions. Use of the compound of the present invention may provide a means to treat such disorders and conditions.

Thus, the compound of the present invention may be suitable for use in the treatment of cell cycling disorders such as cancers, including hormone dependent and hormone independent cancers.

In addition, the compound of the present invention may be suitable for the treatment of cancers such as breast cancer, ovarian cancer, endometrial cancer, sarcomas, melanomas, prostate cancer, pancreatic cancer etc. and other solid tumours.

For some applications, cell cycling is inhibited and/or prevented and/or arrested, preferably wherein cell cycling is prevented and/or arrested. In one aspect cell cycling may be inhibited and/or prevented and/or arrested in the $G_2/M$ phase. In one aspect cell cycling may be irreversibly prevented and/or inhibited and/or arrested, preferably wherein cell cycling is irreversibly prevented and/or arrested.

By the term "irreversibly prevented and/or inhibited and/or arrested" it is meant after application of a compound of the present invention, on removal of the compound the effects of the compound, namely prevention and/or inhibition and/or arrest of cell cycling, are still observable. More particularly by the term "irreversibly prevented and/or inhibited and/or arrested" it is meant that when assayed in accordance with the cell cycling assay protocol presented herein, cells treated with a compound of interest show less growth after Stage 2 of the protocol I than control cells. Details on this protocol are presented below.

Thus, the present invention provides compounds which: cause inhibition of growth of oestrogen receptor positive (ER+) and ER negative (ER−) breast cancer cells in vitro by preventing and/or inhibiting and/or arresting cell cycling; and/or cause regression of nitroso-methyl urea (NMU)-induced mammary tumours in intact animals (i.e. not ovariectomised), and/or prevent and/or inhibit and/or arrest cell cycling in cancer cells; and/or act in vivo by preventing and/or inhibiting and/or arresting cell cycling and/or act as a cell cycling agonist.

Cell Cycling Assay

Protocol 7

Procedure
Stage 1
MCF-7 breast cancer cells are seeded into multi-well culture plates at a density of 105 cells/well. Cells were allowed to attach and grown until about 30% confluent when they are treated as follows:
Control—no treatment
Compound of Interest (COI) 20 μM Cells are grown for 6 days in growth medium containing the COI with changes of medium/COI every 3 days. At the end of this period cell numbers were counted using a Coulter cell counter.
Stage 2
After treatment of cells for a 6-day period with the COI cells are re-seeded at a density of $10^4$ cells/well. No further treatments are added. Cells are allowed to continue to grow for a further 6 days in the presence of growth medium. At the end of this period cell numbers are again counted.
Cancer As indicated, the compounds of the present invention may be useful in the treatment of a cell cycling disorder. A particular cell cycling disorder is cancer.

Cancer remains a major cause of mortality in most Western countries. Cancer therapies developed so far have included blocking the action or synthesis of hormones to inhibit the growth of hormone-dependent tumours. However, more aggressive chemotherapy is currently employed for the treatment of hormone-independent tumours.

Hence, the development of a pharmaceutical for anti-cancer treatment of hormone dependent and/or hormone independent tumours, yet lacking some or all of the side-effects associated with chemotherapy, would represent a major therapeutic advance.

It is known that oestrogens undergo a number of hydroxylation and conjugation reactions after their synthesis. Until recently it was thought that such reactions were part of a metabolic process that ultimately rendered oestrogens water soluble and enhanced their elimination from the body. It is now evident that some hydroxy metabolites (e.g. 2-hydroxy and 16alpha-hydroxy) and conjugates (e.g. oestrone sulphate, E1S) are important in determining some of the complex actions that oestrogens have in the body.

Workers have investigated the formation of 2- and 16-hydroxylated oestrogens in relation to conditions that alter the risk of breast cancer. There is now evidence that factors which increase 2-hydroxylase activity are associated with a reduced cancer risk, while those increasing 16alpha-hydroxylation may enhance the risk of breast cancer. Further interest in the biological role of estrogen metabolites has been stimulated by the growing body of evidence that 2-methoxyoestradiol is an endogenous metabolite with anti-mitotic properties. 2-MeOE2 is formed from 2-hydroxy estradiol (2-OHE2) by catechol estrogen methyl transferase, an enzyme that is widely distributed throughout the body.

Workers have shown that in vivo 2-MeOE2 inhibits the growth of tumours arising from the subcutaneous injection of Meth A sarcoma, B16 melanoma or MDA-MB-435 estrogen receptor negative (ER−) breast cancer cells. It also inhibits endothelial cell proliferation and migration, and in vitro angiogenesis. It was suggested that the ability of 2-MeOE2 to inhibit tumour growth in vivo may be due to its ability to inhibit tumour-induced angiogenesis rather than direct inhibition of the proliferation of tumour cells.

The mechanism by which 2-MeOE2 exerts its potent anti-mitogenic and anti-angiogenic effects is still being elucidated. There is evidence that at high concentrations it can inhibit microtubule polymerisation and act as a weak inhibitor of colchicine binding to tubulin. Recently, however, at concentrations that block mitosis, tubulin filaments in cells were not found to be depolymerised but to have an identical morphology to that seen after taxol treatment. It is possible, therefore, that like taxol, a drug that is used for breast and ovarian breast cancer therapy, 2-MeOE2 acts by stabilising microtubule dynamics.

While the identification of 2-MeOE2 as a new therapy for cancer represents an important advance, the bioavailability of orally administered oestrogens is poor. Furthermore, they can undergo extensive metabolism during their first pass through the liver. As part of a research programme to develop a steroid sulphatase inhibitor for breast cancer therapy, oestrone-3-O-sulphamate (EMATE) was identified as a potent active site-directed inhibitor. Unexpectedly, EMATE proved to possess potent oestrogenic properties with its oral uterotrophic activity in rats being a 100-times higher than that of estradiol. Its enhanced oestrogenicity is thought to result from its absorption by red blood cells (rbcs) which protects it from inactivation during its passage through the liver and which act as a reservoir for its slow release for a prolonged period of time. A number of A-ring modified analogues were synthesised and tested, including 2-methoxyoestrone-3-O-sulphamate. While this compound was equipotent with EMATE as a steroid sulphatase inhibitor, it was devoid of oestrogenicity.

We believe that the compound of the present invention provides a means for the treatment of cancers and, especially, breast cancer.

In addition or in the alternative the compound of the present invention may be useful in the blocking the growth of cancers including leukaemias and solid tumours such as breast, endometrium, prostate, ovary and pancreatic tumours.

Therapy Concerning Oestrogen

We believe that some of the compounds of the present invention may be useful in the control of oestrogen levels in the body—in particular in females. Thus, some of the compounds may be useful as providing a means of fertility control—such as an oral contraceptive tablet, pill, solution or lozenge. Alternatively, the compound could be in the form of an implant or as a patch.

Thus, the compounds of the present invention may be useful in treating hormonal conditions associated with oestrogen.

In addition or in the alternative the compound of the present invention may be useful in treating hormonal conditions in addition to those associated with oestrogen. Hence, the compound of the present invention may also be capable of affecting hormonal activity and may also be capable of affecting an immune response.

Neurodegenerative Diseases

We believe that some of the compounds of the present invention may be useful in the treatment of neurodenerative diseases, and similar conditions.

By way of example, it is believed that STS inhibitors may be useful in the enhancing the memory function of patients suffering from illnesses such as amnesia, head injuries, Alzheimer's disease, epileptic dementia, presenile dementia, post traumatic dementia, senile dementia, vascular dementia and post-stroke dementia or individuals otherwise seeking memory enhancement.

TH1

We believe that some of the compounds of the present invention may be useful in TH1 implications.

By way of example, it is believed that the presence of STS inhibitors within the macrophage or other antigen presenting cells may lead to a decreased ability of sensitised T cells to mount a TH1 (high IL-2, IFNγ low IL-4) response. The normal regulatory influence of other steroids such as glucocorticoids would therefore predominate.

Inflamatory Conditions

We believe that some of the compounds of the present invention may be useful in treating inflammatory conditions—such as conditions associated with any one or more of: autoimmunity, including for example, rheumatoid arthritis, type I and II diabetes, systemic lupus erythematosus, multiple sclerosis, myasthenia gravis, thyroiditis, vasculitis, ulcerative colitis and Crohn's disease, skin disorders e.g. psoriasis and contact dermatitis; graft versus host disease; eczema; asthma and organ rejection following transplantation.

By way of example, it is believed that STS inhibitors may prevent the normal physiological effect of DHEA or related steroids on immune and/or inflammatory responses.

The compounds of the present invention may be useful in the manufacture of a medicament for revealing an endogenous glucocorticoid-like effect.

Other Therapies

It is also to be understood that the compound/composition of the present invention may have other important medical implications.

For example, the compound or composition of the present invention may be useful in the treatment of the disorders listed in WO-A-99/52890—viz:

In addition, or in the alternative, the compound or composition of the present invention may be useful in the treatment of the disorders listed in WO-A-98/05635. For ease of reference, part of that list is now provided: cancer, inflammation or inflammatory disease, dermatological disorders, fever, cardiovascular effects, haemorrhage, coagulation and acute phase response, cachexia, anorexia, acute infection, HIV infection, shock states, graft-versus-host reactions, autoimmune disease, reperfusion injury, meningitis, migraine and aspirin-dependent anti-thrombosis; tumour growth, invasion and spread, angiogenesis, metastases, malignant, ascites and malignant pleural effusion; cerebral ischaemia, ischaemic heart disease, osteoarthritis, rheumatoid arthritis, osteoporosis, asthma, multiple sclerosis, neurodegeneration, Alzheimer's disease, atherosclerosis, stroke, vasculitis, Crohn's disease and ulcerative colitis; periodontitis, gingivitis; psoriasis, atopic dermatitis, chronic ulcers, epidermolysis bullosa; corneal ulceration, retinopathy and surgical wound healing; rhinitis, allergic conjunctivitis, eczema, anaphylaxis; restenosis, congestive heart failure, endometriosis, atherosclerosis or endosclerosis.

In addition, or in the alternative, the compound or composition of the present invention may be useful in the treatment of disorders listed in WO-A-98/07859. For ease of reference, part of that list is now provided: cytokine and cell proliferation/differentiation activity; immunosuppressant or immunostimulant activity (e.g. for treating immune deficiency, including infection with human immune deficiency virus; regulation of lymphocyte growth; treating cancer and many autoimmune diseases, and to prevent transplant rejection or induce tumour immunity); regulation of haematopoiesis, e.g. treatment of myeloid or lymphoid diseases; promoting growth of bone, cartilage, tendon, ligament and nerve tissue, e.g. for healing wounds, treatment of burns, ulcers and periodontal disease and neurodegeneration; inhibition or activation of follicle-stimulating hormone (modulation of fertility); chemotactic/chemokinetic activity (e.g. for mobilising specific cell types to sites of injury or infection); haemostatic and thrombolytic activity (e.g. for treating haemophilia and stroke); antiinflammatory activity (for treating e.g. septic shock or Crohn's disease); as antimicrobials; modulators of e.g. metabolism or behaviour; as analgesics; treating specific deficiency disorders; in treatment of e.g. psoriasis, in human or veterinary medicine.

In addition, or in the alternative, the composition of the present invention may be useful in the treatment of disorders listed in WO-A-98/09985. For ease of reference, part of that list is now provided: macrophage inhibitory and/or T cell inhibitory activity and thus, anti-inflammatory activity; anti-immune activity, i.e. inhibitory effects against a cellular and/or humoral immune response, including a response not associated with inflammation; inhibit the ability of macrophages and T cells to adhere to extracellular matrix components and fibronectin, as well as up-regulated fas receptor expression in T cells; inhibit unwanted immune reaction and inflammation including arthritis, including rheumatoid arthritis, inflammation associated with hypersensitivity, allergic reactions, asthma, systemic lupus erythematosus, collagen diseases and other autoimmune diseases, inflammation associated with atherosclerosis, arteriosclerosis, atherosclerotic heart disease, reperfusion injury, cardiac arrest, myocardial infarction, vascular inflammatory disorders, respiratory distress syndrome or other cardiopulmonary diseases, inflammation associated with peptic ulcer, ulcerative colitis and other diseases of the gastrointestinal tract, hepatic fibrosis, liver cirrhosis or other hepatic diseases, thyroiditis or other glandular diseases, glomerulonephritis or other renal and urologic diseases, otitis or other oto-rhino-laryngological diseases, dermatitis or other dermal diseases, periodontal diseases or other dental diseases, orchitis or epididimo-orchitis, infertility, orchidal trauma or other immune-related testicular diseases, placental dysfunction, placental insufficiency, habitual abortion, eclampsia, pre-eclampsia and other immune and/or inflammatory-related gynaecological diseases, posterior uveitis, intermediate uveitis, anterior uveitis, conjunctivitis, chorioretinitis, uveoretinitis, optic neuritis, intraocular inflammation, e.g. retinitis or cystoid macular oedema, sympathetic ophthalmia, scleritis, retinitis pigmentosa, immune and inflammatory components of degenerative fondus disease, inflammatory components of ocular trauma, ocular inflammation caused by infection, proliferative vitreo-retinopathies, acute ischaemic optic neuropathy, excessive scarring, e.g. following glaucoma filtration operation, immune and/or inflammation reaction against ocular implants and other immune and inflammatory-related ophthalmic diseases, inflammation associated with autoimmune diseases or conditions or disorders where, both in the central nervous system (CNS) or in any other organ, immune and/or inflammation suppression would be beneficial, Parkinson's disease, complication and/or side effects from treatment of Parkinson's disease, AIDS-related dementia complex HIV-related encephalopathy, Devic's disease, Sydenham chorea, Alzheimer's disease and other degenerative diseases, conditions or disorders of the CNS, inflammatory components of stokes, post-polio syndrome, immune and inflammatory components of psychiatric disorders, myelitis, encephalitis, subacute sclerosing pan-encephalitis, encephalomyelitis, acute neuropathy, subacute neuropathy, chronic neuropathy, Guillaim-Barre syndrome, Sydenham chora, myasthenia gravis, pseudo-tumour cerebri, Down's Syndrome, Huntington's disease, amyotrophic lateral sclerosis, inflammatory components of CNS compression or CNS trauma or infections of the CNS, inflammatory components of muscular atrophies and dystrophies, and immune and inflammatory related diseases, conditions or disorders of the central and peripheral nervous systems, post-traumatic inflammation, septic shock, infectious diseases, inflammatory complications or side effects of surgery, bone marrow transplantation or other transplantation complications and/or side effects, inflammatory and/or immune complications and side effects of gene therapy, e.g. due to infection with a viral carrier, or inflammation associated with AIDS, to suppress or inhibit a humoral and/or cellular immune response, to treat or ameliorate monocyte or leukocyte proliferative diseases, e.g. leukaemia, by reducing the amount of monocytes or lymphocytes, for the prevention and/or treatment of graft rejection in cases of transplantation of natural or artificial cells, tissue and organs such as cornea, bone marrow, organs, lenses, pacemakers, natural or artificial skin tissue.

Compound Preparation

The compounds of the present invention may be prepared by reacting an appropriate alcohol with a suitable chloride. By way of example, the sulphamate compounds of the present invention may be prepared by reacting an appropriate alcohol with a suitable sulfamoyl chloride, of the formula $R^4R^5NSO_2Cl$.

Typical conditions for carrying out the reaction are as follows.

Sodium hydride and a sulfamoyl chloride are added to a stirred solution of the alcohol in anhydrous dimethyl formamide at 0° C. Subsequently, the reaction is allowed to warm to room temperature whereupon stirring is continued for a further 24 hours. The reaction mixture is poured onto a cold saturated solution of sodium bicarbonate and the resulting aqueous phase is extracted with dichloromethane. The combined organic extracts are dried over anhydrous $MgSO_4$. Filtration followed by solvent evaporation in vacuo and co-evaporated with toluene affords a crude residue which is further purified by flash chromatography.

Preferably, the alcohol is derivatised, as appropriate, prior to reaction with the sulfamoyl chloride. Where necessary, functional groups in the alcohol may be protected in known manner and the protecting group or groups removed at the end of the reaction.

Preferably, the sulphamate compounds are prepared according to the teachings of Page et al (1990 Tetrahedron 46; 2059-2068).

The phosphonate compounds may be prepared by suitably combining the teachings of Page et al (1990 Tetrahedron 46; 2059-2068) and PCT/GB92/01586.

The sulphonate compounds may be prepared by suitably adapting the teachings of Page et al (1990 Tetrahedron 46; 2059-2068) and PCT/GB92/01586.

The thiophosphonate compounds may be prepared by suitably adapting the teachings of Page et al (1990 Tetrahedron 46; 2059-2068) and PCT/GB91/00270.

Preferred preparations are also presented in the following text.

SUMMARY

In summation, the present invention provides novel compounds for use as steroid sulphatase inhibitors and/or aromatase inhibitors and/or modulators of apoptosis and/or modulators of cell cycling and/or cell growth, and pharmaceutical compositions containing them.

EXAMPLES

The present invention will now be described in further detail by way of example only with reference to the accompanying figure in which:—

FIG. 1 shows a summary scheme; and

FIG. 2 shows a summary scheme.

The present invention will now be described only by way of example. However, it is to be understood that the examples also present preferred compounds of the present invention, as well as preferred routes for making same and useful intermediates in the preparation of same.

Synthetic Routes

Compounds in accordance with the present invention were synthesised in accordance with the synthetic routes and schemes.

Experimental 3,3'-Dihydroxybenzophenone
(MW01012/PMW01016)

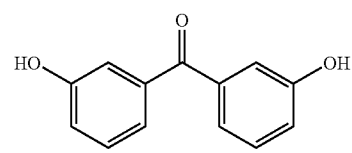

This was prepared as described by Wittig et al. [*Chem. Berichte*, 1947, 363].

Bis-(3-hydroxyphenyl)methanol (MW01015/PMW01019)

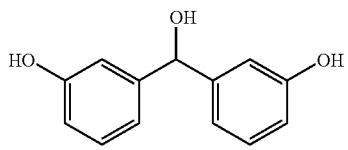

A solution of sodium borohydride (NaBH$_4$) (0.19 g, 5.14 mmol) in H$_2$O (5 mL) was added to an orange solution of 3,3'-dihydroxybenzophenone (1.00 g, 4.67 mmol) in EtOH (15 mL) and the resulting mixture was stirred for 1 h. After this time, the reaction mixture was added to ice-water (40 mL) containing conc. HCl (2.5 mL) and the solution was extracted with EtOAc (2×60 mL). The combined organic layers were washed with NaOH (3M, 2×50 mL) and the combined basic washes were acidified with conc. HCl. The organic components that appeared were extracted with EtOAc (2×100 mL). The combined EtOAc extracts were dried (MgSO$_4$) and the solvent was removed in vacuo to give the crude product as a brown oil which solidified on standing. Purification was achieved by recrystallisation from H$_2$O to give the title compound as a brown crystalline solid (0.86 g, 85%, mp 141-142° C.); $\delta_H$ (270 MHz, d$^6$-DMSO) 9.27 (2H, br s, ArOH), 7.05 (2H, t, J=8.2, ArH), 6.84-6.72 (4H, m, ArH), 6.63-6.54 (2H, m, ArH), 5.72 (1H, br s, CHOH), 5.50 (1H, s, CHOH); $\delta_C$ (68 MHz, d$^6$-DMSO) 157.1 (2×C), 147.2 (2×C), 128.9 (2×CH), 117.0 (2×CH), 113.6 (2×CH), 113.1 (2×CH), 74.1 (CH); LCMS (ES$^-$) 215.0 ([M−H]$^-$, 30%), 196.9 (10), 168.8 (15), 120.7 (100); HRMS (FAB$^+$) Found 216.0785, C$_{13}$H$_{12}$O$_3$ requires 216.0786.

1-[Bis-(3-hydroxyphenyl)methyl]-1H-[1,2,4]triazole (PW01018/PMW01021, STX951)

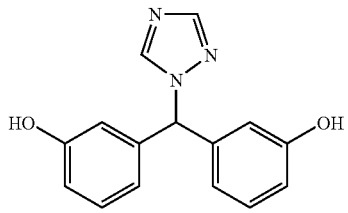

Bis-(3-hydroxyphenyl)methanol (0.75 g, 3.47 mmol), 1,2,4-triazole (0.48 g, 6.94 mmol), p-TSA (125 mg) and toluene (300 mL) were dissolved/suspended in toluene and heated at reflux with a Dean-Stark separator for 24 h. The reaction mixture was allowed to cool, and the solvent was removed in vacuo. The resulting residue was dissolved in EtOAc (75 mL) and the organic layer was washed with H$_2$O (3×75 mL), dried (MgSO$_4$) and the solvent was removed in vacuo to give a brown solid. The crude product was purified by flash column chromatography (EtOAc:Hexane 3:1) to give the title compound (0.82 g, 88%) as a pale yellow oil which formed a foam after a prolonged period under high vacuum; $\delta_H$ (270 MHz, d$^6$-DMSO) 9.50 (2H, br s, ArOH), 8.55 (1H, s, NCHN), 8.06 (1H, s, NCHN), 7.16 (2H, t, J=7.9, ArH), 6.89 (1H, s, CH), 6.75-6.68 (2H, m, ArH), 6.67-6.60 (4H, m, ArH); $\delta_C$ (100 MHz, d$^6$-DMSO) 158.0 (2×C), 152.3 (CH), 144.9 (CH), 141.0 (2×C), 130.2 (2×CH), 119.3 (2×CH), 115.6 (2×CH), 115.6 (2×CH), 66.2 (CH); LRMS (FAB$^+$) 268.3 ([M+H]$^+$, 100%), 199.2 (85); HRMS (FAB$^+$) Found 268.1091, C$_{15}$H$_{14}$N$_3$O$_2$ requires 268.1086; HPLC (CH$_3$CN/H$_2$O, 90:10) t$_R$=1.79 min (purity: 99+%).

1-[Bis-(3-sulphamoyloxyphenyl)methyl]-1H-[1,2,4]triazole (PMW01023, STX1001)

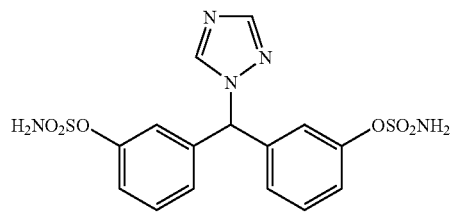

A solution of sulphamoyl chloride (H$_2$NSO$_2$Cl) in toluene (0.7 M, 8.8 mL) was concentrated in vacuo at 30° C. to furnish a yellow oil which solidified upon cooling in an ice bath. DMA (7 mL) and STX951 (0.30 g, 1.12 mmol) were subsequently added and the mixture was allowed to warm to room temperature and stirred overnight. The resulting yellow solution was added to brine (30 mL) and this was extracted with EtOAc (3×50 mL). The organic layers were combined, washed with H$_2$O (3×50 mL), dried (MgSO$_4$) and the solvent was removed in vacuo. The crude product was purified by flash column chromatography (CHCl$_3$:Acetone 1:1) to give the title compound STX1001 (0.42 g, 88%) as a pale yellow oil which formed a foam after a prolonged period under high vacuum; $\delta_H$ (270 MHz, d$^6$-DMSO) 8.64 (1H, s, NCHN), 8.11 (1H, s, NCHN), 8.04 (4H, br s, 2×NH$_2$), 7.49 (2H, t, J=7.9, ArH), 7.36-7.16 (7H, m, ArH and CH); $\delta_C$ (100 MHz, d$^6$-DMSO) 152.7 (2×C), 150.7 (CH), 145.2 (2×C), 140.9 (CH), 130.6 (2×CH), 126.8 (2×CH), 122.4 (4×CH), 64.8 (CH); LRMS (FAB$^+$) 426.0 ([M+H]$^+$, 100%), 357.0 (50), 85.1 (50); HRMS (FAB$^+$) Found 426.0540, C$_{15}$H$_{16}$N$_5$O$_6$S$_2$ requires 426.0542; HPLC (CH$_3$CN/H$_2$O, 90:10) t$_R$=1.50 min (purity: 99+%).

5-Bromo-2-methoxyphenol

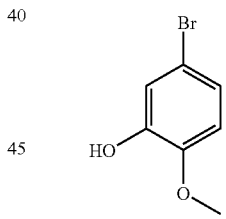

This was prepared as described by Van der May et al [J. Med. Chem 2001, 44, 2523].

2-Benzyloxy-4-bromo-1-methoxybenzene (PMW01028)

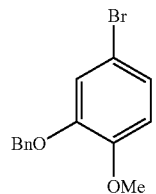

NaH, 60% dispersion in mineral oil (0.61 g, 15.3 mmol) was added in three equal portions to DMF (25 mL) pre-cooled to 0° C. 5-Bromo-2-methoxyphenol (2.60 g, 12.8 mmol) was then added in three portions, and the resulting brown solution was stirred for 20 min. Benzyl bromide (2.63 g, 15.3 mmol)

was added and the reaction mixture was allowed to warm to room temperature and was stirred overnight resulting in the formation of a yellow solution. The reaction mixture was poured onto H$_2$O (40 mL) leading to the formation of a white precipitate which was extracted into EtOAc (4×50 mL). The combined organics were washed with H$_2$O (4×75 mL), brine (75 mL), dried (MgSO$_4$) and the solvent was removed in vacuo. The crude product was obtained as a white solid which was purified by recrystallisation from Et$_2$O to give the title compound (2.90 g, 77%, mp 109-110° C. [lit. 105-106° C. (Et$_2$O)]$^{Aust.\ J.\ Chem.,\ 1981,34\ 587}$) as a white crystalline solid; $\delta_H$ (270 MHz, CDCl$_3$) 7.47-7.26 (5H, m, ArH), 7.07-7.00 (2H, m, ArH), 6.74 (1H, d, J=8.7, ArH), 5.10 (2H, s, CH$_2$), 3.85 (3H, s, CH$_3$), LRMS (FAB$^+$) 294.0 ([M+H]$^+$, 35%), 292.0 (35), 91.1 (100).

Bis-(3-benzyloxy-4-methoxyphenyl)methanol
(PMO01033/PMW01035)

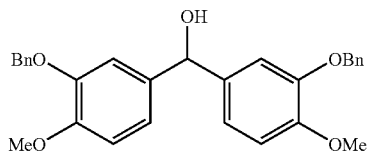

n-BuLi (1.6 M, 5.2 mL) was added to a solution of 2-benzyloxy-4-bromo-1-methoxybenzene (2.10 g, 7.2 mmol) in THF (28 mL) at −78° C. and the resulting yellow solution was stirred at this temperature for 1 h. A solution of 3-benzyloxy-4-methoxybenzaldehyde (1.74 g, 7.2 mmol) in THF (16 mL) was added dropwise at −78° C. and the reaction mixture was stirred at this temperature for 1.5 h and then at room temperature for 2 h. Water (100 mL) was added to the yellow solution and the resulting mixture was extracted with EtOAc (3×100 mL). The combined organics were dried (MgSO$_4$), and solvent was removed in vacuo to give a thick yellow oil which solidified after standing overnight. The crude product was purified by precipitation from EtOAc/hexane to give the title compound (1.70 g, 52%, mp 103-105° C.) as a white solid; $\delta_H$ (270 MHz, CDCl$_3$) 7.42-7.21 (10H, m, ArH), 6.89-6.79 (6H, m, ArH), 5.63 (1H, d, J=3.5, CHOH), 5.06 (4H, s, 2×CH$_2$), 3.86 (6H, s, 2×CH$_3$), 2.02 (1H, d, J=3.5, CHOH); $\delta_C$ (100 MHz, d$^6$-DMSO) 149.2 (2×C), 148.2 (2×C), 137.2 (2×C), 136.6 (2×C), 128.7 (4×CH), 128.0 (2×CH), 127.6 (4×CH), 119.5 (2×CH), 112.6 (2×CH), 111.7 (2×CH), 75.8 (CH), 71.2 (2×CH$_2$), 56.4 (2×CH$_3$); LRMS (FAB$^+$) 456.1 (M$^+$, 45%), 439.1 (85), 349.2 (10), 243.1 (20), 91.1 (100); HRMS (FAB$^+$) Found 456.1944, C$_{29}$H$_{28}$O$_5$ requires 456.1937.

1-[Bis-(3-benzyloxy-4-methoxyphenyl)methyl]-1H-[1,2,4]triazole (PMW01036/PMW01041)

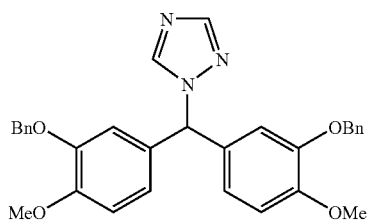

Bis-(3-benzyloxy-4-methoxyphenyl)methanol (1.60 g, 3.50 mmol), 1,2,4-triazole (0.48 g, 6.95 mmol) and p-TSA (160 mg) dissolved/suspended in toluene (230 mL) were heated at reflux with a Dean-Stark separator for 24 h. The reaction mixture was allowed to cool, and the solvent was removed in vacuo. The resulting residue was dissolved in EtOAc (100 mL) and the organic layer was washed with H$_2$O (3×100 mL), dried (MgSO$_4$) and the solvent was removed in vacuo. The crude product was purified using Flashmaster II (EtOAc/Hexane) to give the title compound (1.51 g, 84%, mp 96-99° C.) as a yellow oil which solidified after standing for a prolonged period; $\delta_H$ (400 MHz, CDCl$_3$) 7.95 (1H, s, NCHN), 7.67 (1H, s, NCHN), 7.34-7.24 (10H, m, ArH), 6.81 (2H, d, J=8.4, ArH), 6.58-6.48 (5H, m, ArH), 5.00 (4H, s, 2×CH$_2$), 3.84 (6H, s, 2×CH$_3$); $\delta_C$ (100 MHz, CDCl$_3$) 152.3 (CH), 149.9 (2×C), 148.2 (2×C), 143.4 (CH), 136.7 (2×C), 130.5 (2×C), 128.7 (4×CH), 128.1 (2×CH), 127.5 (4×CH), 121.1 (2×CH), 114.1 (2×CH), 118.8 (2×CH), 71.2 (2×CH$_2$), 67.4 (CH), 56.4 (2×CH$_3$); LRMS (FAB$^+$) 507.2 (M$^+$, 20%), 439.2 (100), 349.2 (15), 257.2 (15), 91.1 (35); HRMS (FAB$^+$) Found 507.2159, C$_{31}$H$_{29}$N$_3$O$_4$ requires 507.2158; Found: C, 73.00%; H, 5.73%; N, 8.31%, C$_{31}$H$_{29}$N$_3$O$_4$ requires: C, 73.35%; H, 5.76%; N, 8.28%.

1-[Bis-(3-hydroxy-4-methoxyphenyl)methyl]-1H-[1,2,4]triazole (PMW01048 STX1003)

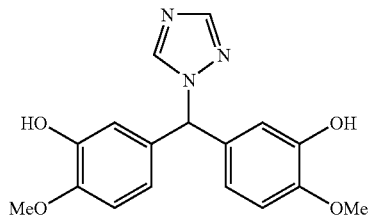

10% Pd/C (80 mg) was added to a solution of 1-[bis-(3-benzyloxy-4-methoxyphenyl)methyl]-1H-[1,2,4]triazole (1.65 g, 3.25 mmol) in THF/MeOH (1:1, 200 mL). The solution was stirred under an atmosphere of H$_2$ (provided by addition from a balloon) overnight. The excess H$_2$ was removed and the reaction mixture was filtered through Celite® washing with THF and MeOH, then the solvent was removed in vacuo. The crude product was purified using Flashmaster II (EtOAc/Hexane) to give the title compound STX1003 (0.86 g, 81%, mp 217.5-219° C.) as a white solid; $\delta_H$ (270 MHz, d$^6$-DMSO) 9.08 (2H, s, 2×OH), 8.47 (1H, s, NCHN), 8.03 (1H, s NCHN), 6.88 (2H, d, J=8.4, ArH), 6.76 (1H, s, CH), 6.64 (2H, s, ArH), 6.57 (2H, d, J=8.4, ArH), 3.74 (6H, s, 2×CH$_3$); $\delta_C$ (68 MHz, d$^6$-DMSO) 151.8 (CH), 147.3 (2×C), 146.3 (2×C), 144.0 (CH), 130.1 (2×C), 118.8 (2×CH), 115.3 (2×CH), 111.9 (2×CH), 64.9 (CH), 55.6 (2×Ch$_3$); LCMS (ES$^-$) 326.2 ([M−H]$^-$, 100%), 255.9 (70), 240.4 (60), 211.4 (70); HRMS (FAB$^+$) Found 327.1226, C$_{17}$H$_{17}$N$_3$O$_4$ requires 327.1219; HPLC (CH$_3$CN/H$_2$O, 90:10) t$_R$=1.57 min 99+%); Found: C, 62.10%, H, 5.26%; N, 12.80%, C$_{17}$H$_{17}$N$_3$O$_4$ requires: C, 62.38%; H, 5.23%; N, 12.84%.

1-[Bis-(3-sulphamoyloxy-4-methoxyphenyl)methyl]-1H-[1,2,4]triazole (PMW01050 STX1007)

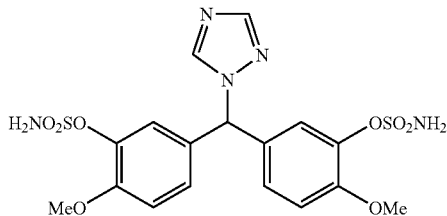

A solution of sulphamoyl chloride (H₂NSO₂Cl) in toluene (0.7 M, 5.8 mL) was concentrated in vacuo at 30° C. to furnish a yellow oil which solidified upon cooling in an ice bath. DMA (6 mL) and STX1003 (0.30 g, 0.92 mmol) were subsequently added and the mixture was allowed to warm to room temperature and stirred overnight. The resulting mixture was poured onto brine (50 mL) and this was extracted with EtOAc (3×50 mL). The organic layers were combined, washed with H₂O (2×50 mL) and brine (2×50 mL), dried (MgSO₄) and the solvent was removed in vacuo. The crude product was purified using Flashmaster II (EtOAc/Hexane) to give the title compound STX1007 (0.40 g, 90%) as a white foam; $\delta_H$ (270 MHz, d⁶-DMSO), 8.56 (1H, s, NCHN), 8.07 (1H, s, NCHN), 7.93 (4H, br s, 2×NH₂), 7.26-7.07 (6H, m, ArH), 7.00 (1H, s, CH), 3.80 (6H, s, 2×CH₃); $\delta_C$ (68 MHz, d⁶-DMSO) 151.8 (CH), 151.6 (2×C), 144.3 (CH), 138.4 (2×C), 131.0 (2×C), 127.1 (2×CH), 123.3 (2×CH), 113.4 (2×CH), 63.9 (CH), 56.0 (2×CH₃); LRMS (FAB⁺) 486.1 ([M+H]⁺, 20%), 417.0 (100), 338.1 (14), 257.1 (6); HRMS (FAB⁻) Found 485.0659, $C_{17}H_{19}N_5O_8S_2$ requires 485.0675; HPLC (CH₃CN/H₂O, 90:10) $t_R$=1.48 min (purity: 99+%).

4-[(3-Benzyloxybenzyl)(4-cyanophenyl)amino]-4H-[1,2,4]triazole

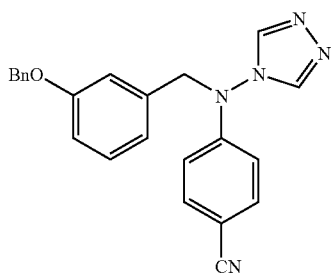

To a stirred suspension of NaH (60% dispersion in oil, 0.22 g, 5.4 mmol) in anhydrous DMF (5 mL) was added a solution of 4-[(4-cyanophenyl)amino]-4H-[1,2,4]triazole (1.0 g, 5.68 mmol) in anhydrous DMF (3 mL) and the mixture stirred at r.t. for 0.5 h. A solution of 3-benzyloxybenzyl bromide[Thakkar 1993] (1.57 g, 5.66 mmol) in anhydrous DMF (2 mL) was then added and the mixture heated at 80-90° C. overnight. The mixture was cooled, diluted with EtOAc (50 mL), washed with water (4×100 mL), brine (100 mL) and dried (Na₂SO₄). Concentration in vacuo an orange residue which was purified by chromatography [SiO₂, EtOAc/n-hexane (1:1)] and to give 4-[(3-benzyloxybenzyl)(4-cyanophenyl)amino]-4H-[1,2,4]triazole as a colourless solid (0.58 g, 28%) after crystallisation; $\delta_H$ (400 MHz, CDCl₃) 4.85 (s, 2H), 5.03 (s, 2H); 6.62 (AA'BB', 2H), 6.77 (d, J=7.8, 1H), 6.79 (d, J=2.4, 1H), 6.96 (dd, J=7.8, 2.4, 1H), 7.26 (t, J=7.8, 1H), 7.34-7.37 (m, 5H), 7.57 (AA'BB', 2H), 8.04 (s, 2H); LC-MS (APCI+) $t_R$=6.81 min, m/z=382 (M+H); HPLC $t_R$=2.27 min (98%).

Thakkar et al., *J. Med. Chem.* 1993, 36, 2950-2955.

4-[(3-Hydroxybenzyl)(4-cyanophenyl)amino]-4H-[1,2,4]triazole (STX333)

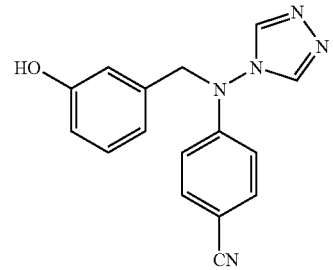

To a solution of 4-[(3-Benzyloxybenzyl)(4-cyanophenyl)amino]-4H-[1,2,4]triazole (0.4 g, 1.05 mmol) in anhydrous THF/MeOH (20 mL) was added Pd—C (10% by wt., 0.04 g). The black suspension was then stirred under an atmosphere of hydrogen (balloon) for 16 h. The catalyst was removed by filteration through Celite® and exhaustively washed with THF. The filtrate was concentrated in vacuo to give a beige residue. Recrystallisation from EtOH gave STX333 as a colourless solid (0.27 g, 88%) after recrystallisation; $\delta_H$ (400 MHz, DMSO-d₆) 4.97 (s, 2H), 6.68 (AA'BB', 2H), 6.72-6.75 (m, 3H), 7.11 (m, 1H), 7.76 (AA'BB', 2H), 8.77 (s, 2H), 9.49 (br s, 1H—exchanges with D₂O); LRMS (FAB+) m/z (rel. intensity) 292 (100%, [M+H]), 223 (42, [M+H-triazole]); HPLC $t_R$=2.22 min, (96%); HRMS (FAB+) Found 292.1198; $C_{16}H_{13}N_5O$ requires 292.1192;

4-[(3-O-Sulfamoylbenzyl)(4-cyanophenyl)amino]-4H-[1,2,4]triazole (STX334)

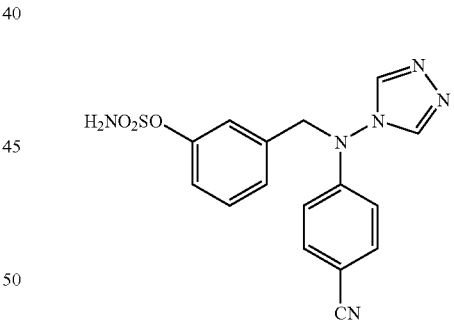

To an ice-cooled solution of STX333 (0.1 g, 0.34 mmol) in anhydrous DMA (2 mL) was added sulfamoyl chloride (0.59 M solution in toluene, 1.2 mL—the toluene was removed in vacuo [not allowing the temperature of the water bath to exceed 30° C.] prior to addition, 0.69 mmol) and the mixture stirred (under a positive flow of dry nitrogen) overnight. The mixture was diluted with EtOAc (25 mL), washed with water (3×50 mL) and brine (50 mL) and concentrated in vacuo (not allowing the temperature of the water bath to exceed 30° C.). The residue was gave STX334 as a colourless solid (0.06 g, 47%) after crystallisation from CH₂Cl₂/acetone; $\delta_H$ (400 MHz, DMSO-d₆) 5.11 (s, 2H), 6.74 (AA'BB', 2H), 7.20-7.27 (m, 3H), 7.40 (1H, t, J=7.8), 7.77 (AA'BB', 2H), 7.98 (br s, 2H—exchanges with D₂O), 8.81 (s, 2H); LRMS (FAB+) m/z (rel. intensity) 371 (100%, [M+H]), 302 (28, [M+H-triazole]); HPLC $t_R$=2.13 min (99%); HRMS (FAB+) Found 371.0926; $C_{16}H_{15}N_6O_3S$ requires 371.0946.

3-Benzoyloxy-4-fluorotoluene

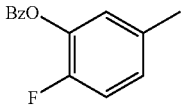

To a solution of 4-fluoro-3-hydroxytoluene (3.784 g, 30 mmol)) in $CH_2Cl_2$ (50 mL) was added $NEt_3$ (5 mL) and the mixture stirred at room temperature for 0.5 h. Benzoyl chloride (4.22 mL, 30 mmol) was then added and the reaction stirred at room temperature for 18 h. The reaction was concentrated in vacuo and the residue redissolved in $Et_2O$ (200 mL), washed with water (100 mL), 2N NaOH (2×30 mL) and brine (20 mL). The ethereal layer was dried ($Na_2SO_4$) and concentrated in vacuo to give 3-benzoyloxy-4-fluorotoluene as a white solid (6.601 g, 96%), which was used without futher purification. $\delta_H$ (400 MHz, $CDCl_3$) 2.36 (s, 3H), 7.01-7.12 (m, 3H), 7.49-7.55 (m, 2H), 7.63-7.68 (m, 1H), 8.19-8.23 (m, 2H); LRMS (FAB+) m/z (rel. intensity) 231.1 (100, $[M+H]^+$)

3-Benzoyloxy-4-fluorobenzyl bromide

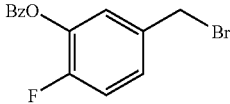

Nb. Commercial N-bromosuccinimide (NBS) was recrystallised from water and thoroughly dried in vacuo (24 h) prior to use (mp. 180-182° C., lit. 180-183° C.). To a solution of 3-benzoyloxy-4-fluorotoluene (2.47 g, 10 mmol) in anhydrous carbon tetrachloride (25 mL) was added finely powdered NBS (1.96 g, 11 mmol) and benzoylperoxide (0.01 g). The mixture heated at reflux for 2 h, cooled and diluted with $Et_2O$ (100 mL) and water (50 mL). The ethereal layer was washed with brine (20 mL) and dried ($Na_2SO_4$). Concetration in vacuo and subsequent purification by flash column chromatography [$SiO_2$, EtOAc/n-hexane (1:25)] gave 3-benzoyloxy-4-fluorobenzyl bromide as a white solid (1.80 g, 58%); $\delta_H$ (400 MHz, $CDCl_3$) 4.48 (s, 2H), 7.18 (dd, J=9.8, 8.6, 1H), 7.28 (ddd, J=8.6, 4.3, 2.3, 1H), 7.34 (dd, J=7.0, 2.3, 1H), 7.50-7.55 (m, 2H), 7.64-7.69 (m, 1H), 8.18-8.23 (m, 2H); LRMS (FAB+) m/z (rel. intensity) 229.1 (95), 309.0 (100, $[M+H]^+$). Found: C, 54.1, H, 3.22; $C_{14}H_{10}BrFO_2$ requires C, 54.39, H, 3.26%.

4-[(3-Benzoyloxy-4-fluorobenzyl)(4-cyanophenyl)amino]-4H-[1,2,4]triazole

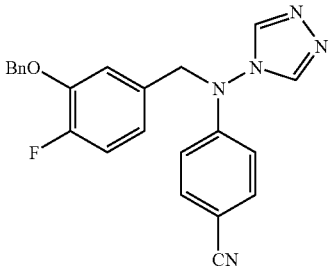

The title compound was prepared by adapting the method for 4-[(3-benzyloxybenzyl)(4-cyanophenyl)amino]-4H-[1,2,4]triazole using NaH (60% dispersion in oil, 0.20 g, 5.0 mmol), 4-[(4-cyanophenyl)amino]-4H-[1,2,4]triazole (0.926 g, 5.0 mmol) and 3-benzoyloxy-4-fluorobenzyl bromide (1.55 g, 5.0 mmol) in anhydrous DMF (20 mL) to give 4-[(3-benzoyloxy-4-fluorobenzyl)(4-cyanophenyl)amino]-4H-[1,2,4]triazole as a white solid (1.16 g, 56%) after chromatography [$SiO_2$, EtOAc (100%)]; $\delta_H$ (400 MHz, $CDCl_3$) 4.91 (s, 2H), 6.67 (AA'BB', 2H), 7.07 (ddd, J=8.2, 4.3, 2.0, 1H), 7.18 (dd, J=9.4, 8.6, 1H), 7.24 (dd, J=7.0, 2.3, 1H), 7.49-7.56 (m, 2H), 7.58 (AA'BB', 2H), 7.62-7.70 (m, 1H), 8.15-8.20 (m, 2H), 8.21 (s, 2H); LRMS (FAB+) m/z (rel. intensity) 414.2 (100, $[M+H]^+$).

4-[(4-Fluoro-3-hydroxybenzyl)(4-cyanophenyl)amino]-4H-[1,2,4]triazole (STX488)

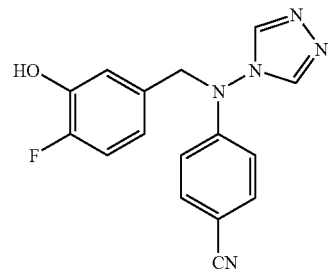

To a solution of 4-[(3-benzoyloxy-4-fluorobenzyl)(4-cyanophenyl)amino]-4H-[1,2,4]triazole (0.958 g, 2.32 mmol) in MeOH (10 mL) was added NaOH (0.25 g, 6.25 mmol), and the solution heated to reflux for 5 minutes and then concentrated in vacuo. Water (10 mL) was added and the milky suspension was neutralised (pH 7-8) with 2N HCl. The white precipitate was filtered off, washed with a small amount of water (5 mL) and dried under high vacuum to give STX488 as a white solid (0.476 g, 66%); $\delta_H$ (400 MHz, DMSO-$d_6$) 4.95 (s, 2H), 6.70 (ddd, J=11.4, 8.4, 2.4, 1H), 6.75 (AA'BB', 2H), 6.84 (dd, J=8.4, 2.4, 1H), 7.06 (dd, J=11.3, 8.4, 1H), 7.76 (AA'BB', 2H), 8.75 (s, 2H), 9.90 (s, 1H—exchanges with $D_2O$); LRMS (FAB+) m/z (rel. intensity) 310.1 (100, $[M+H]^+$).

Sulfamic acid 5-{[(4-cyano-phenyl)-[1,2,4]triazol-4-yl-amino]-methyl}-2-fluoro-phenyl ester (CABO3149/STX1122)

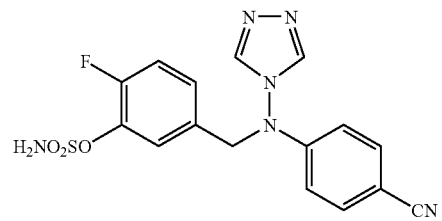

Sulphamoyl chloride solution in toluene (3 ml, 0.7 M, 2.1 mmol) was concentrated under reduced pressure (30° C. water bath temperature) to ca. 0.5 ml volume. The residue was cooled to 0° C. (ice bath) and N,N-dimethyl acetamide (5 ml) was added. 4-[(4-Fluoro-3-hydroxybenzyl)-[1,2,4]triazol-4-yl-amino]-benzonitrile (STX488, 155 mg, 0.50 mmol) was added to the colourless solution and the mixture was stirred for 4 hours at room temperature. Ethyl acetate (50 ml) and water (30 mL) were added to the solution, the organic layer was separated, washed with water (2×30 ml) and brine (1×20 ml), dried over sodium sulphate and concentrated under reduced pressure. The residue was dissolved in acetone (5 ml) and precipitated by addition of diethyl ether. The precipitate (STX1122) was filtered off and dried under high vacuum.

Yield: 157 mg (83%) white powder. $^1$H-NMR (400 MHz, DMSO-d$_6$) δ5.07 (s, 2H), 6.74 (d, J=8.9 Hz, 2H), 7.20-7.26 (m, 1H), 7.33 (dd, J=10.1, 8.6 Hz, 1H), 7.38 (dd, J=7.4, 2.3 Hz, 1H), 7.75 (d, J=8.9 Hz, 2H), 8.25 (s, 2H, —NH$_2$), 8.77 (s, 2H); MS (FAB+): m/z 389.0 (100%, [C$_{16}$H$_{13}$FN$_6$O$_3$S$_2$+H]$^+$); HRMS (FAB+) for C$_{16}$H$_{14}$FN$_6$O$_3$S: 389.08321; found, 389.08300; HPLC t$_R$=1.763 min (100%); Anal. (C$_{16}$H$_{13}$FN$_6$O$_3$S) C, H, N;

Calculated: N, 21.64% C, 49.48% H, 3.37% Result: N, 21.1% C, 49.3% H, 3.39%

3-Benzoyloxy-4-chlorotoluene

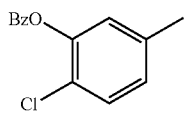

The title compound was prepared by adapting the method for 3-benzoyloxy-4-fluorotoluene using 4-chloro-3-hydroxytoluene (3.92 g, 27.5 mmol), benzoyl chloride (3.51 g, 25 mmol) and NEt$_3$ (5 mL) in CH$_2$Cl$_2$ (100 mL) to give 3-benzoyloxy-4-chlorotoluene as a white solid (5.82 g, 94%), which was used without further purification. δ$_H$ (400 MHz, CDCl$_3$) 2.38 (s, 3H,), 7.05 (d, J=8.2, 1H), 7.11 (s, 1H), 7.36 (d, J=8.2, 1H), 7.51-7.56 (m, 2H), 7.64-7.70 (m, 1H), 8.22-8.28 (m, 2H); δ$_C$ (100 MHz, CDCl$_3$) 21.41, 123.97, 124.58, 128.07, 128.85, 129.15, 130.07, 130.55, 134.01, 138.38, 146.98, 164.51.

3-Benzoyloxy-4-chlorobenzyl bromide

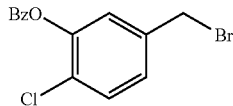

The title compound was prepared by adapting the method for 3-benzoyloxy-4-fluorobenzyl bromide using 3-benzoyloxy-4-chlorotoluene (2.47 g, 10.0 mmol), NBS (1.96 g, 11.0 mmol) and benzoyl peroxide (10 mg) in carbon tetrachloride (25 mL). The residue was purified by flash column chromatography [SiO$_2$, EtOAc/n-hexane (1:40)] to give 3-benzoyloxy-4-chlorobenzyl bromide as a colourless oil (2.012 g, 62%) which solidified on standing and was used without further purification; δ$_H$ (400 MHz, CDCl$_3$) 4.48 (s, 2H), 7.27 (dd, J=8.2, 2.0, 1H), 7.36 (d, J=2.0, 1H), 7.46 (d, J=8.2, 1H), 7.50-7.58 (m, 2H), 7.64-7.71 (m, 1H), 8.22-8.28 (m, 2H). LRMS (FAB+) m/z (rel. intensity) 325.0 (81, [M+H]$^+$), 327.0 (100, [M+H]$^+$);

4-[(3-Benzoyloxy-4-chlorobenzyl)(4-cyanophenyl)amino]-4H-[1,2,4]triazole

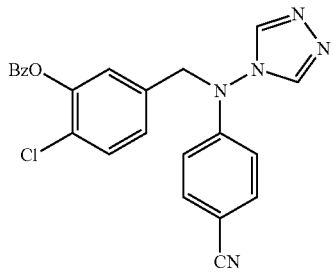

The title compound was prepared by adapting the method for 4-[(3-benzyloxybenzyl)(4-cyanophenyl)amino]-4H-[1,2,4]triazole using NaH (60% dispersion in oil, 0.20 g, 5.0 mmol), 4-[(4-cyanophenyl)amino]-4H-[1,2,4]triazole (0.926 g, 5.0 mmol) and 3-benzoyloxy-4-chlorobenzyl bromide (1.63 g, 5.0 mmol) in anhydrous DMF (20 mL) to give 4-[(3-benzoyloxy-4-chlorobenzyl)(4-cyanophenyl)amino]-4H-[1,2,4]triazole as a white solid (1.773 g, 82%) after chromatography [SiO$_2$, EtOAc (100%)]; δ$_H$ (400 MHz, CDCl$_3$) 4.93 (s, 2H), 6.66 (AA'BB', 2H), 7.06 (dd, J=8.2, 2.0, 1H), 7.27 (d, J=2.0, 1H), 7.45 (d, J=8.2, 1H), 7.47-7.58 (m, 4H), 7.60-7.69 (m, 1H), 8.16-8.21 (m, 2H), 8.24 (s, 2H); LRMS (FAB+) m/z (rel. intensity) 430.1 (100, [M+H]$^+$).

4-[(4-Chloro-3-hydroxybenzyl)(4-cyanophenyl)amino]-4H-[1,2,4]triazole (STX483)

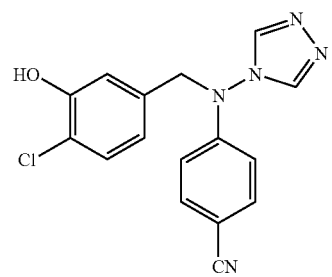

A solution of 4-[(3-benzoyloxy-4-chlorobenzyl)(4-cyanophenyl)amino]-4H-[1,2,4]triazole (1.13 g, 2.63 mmol) and NaOMe (500 mg) in MeOH (20 mL) and water (5 mL) was heated to reflux for 30 minutes. After cooling to room temperature most of the solvent was removed in vacuo and concentrated sodium bicarbonate solution (20 mL) and EtOAc (50 mL) were added. The organic layer was separated, dried (Na$_2$SO$_4$) and the solvent was removed under reduced pressure. The resulting white powder was refluxed in EtOAc (10 mL, product did not dissolve completely). The product was filtered off and dried in vacuo to give STX483 as a white powder (0.412 g, 48%); δ$_H$ (400 MHz, DMSO-d6) 4.97 (s, 2H), 6.71-6.75 (m, 3H, AA'BB' and ArH), 6.84 (d, J=2.0, 1H), 7.25 (d, J=8.2, 1H), 7.75 (AA'BB', 2H), 8.76 (s, 2H), 10.21 (s, 1H—exchanges with D$_2$O); LRMS (FAB+) m/z (rel. intensity) 326.1 (100, [M+H]$^+$).

4-[(4-Chloro-3-O-sulfamoylbenzyl)(4-cyanophenyl)amino]-4H-[1,2,4]triazole (STX559)

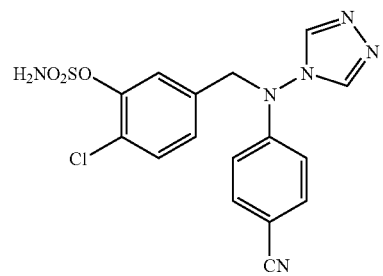

The title compound was sulfamoylated adapting the method for STX334 using STX483 (0.2 g, 0.614 mmol) and sulfamoyl chloride (0.7 M solution toluene, 3 mL, 2.1 mmol) in anhydrous DMA (5 mL) to give STX559 as a white powder (0.136 g, 55%) after precipitation from acetone/Et$_2$O; δ$_H$ (400 MHz, DMSO-d$_6$) 5.11 (s, 2H), 6.75 (AA'BB', 2H), 7.25 (dd, J=8.2, 2.0, 1H), 7.46 (d, J=2.0, 1H), 7.54 (d, J=8.2, 1H), 7.77 (AA'BB', 2H), 8.32 (s, 2H—exchanges with D$_2$O), 8.82 (s, 2H); LRMS (FAB+) m/z (rel. intensity) 87.0 (100), 404.9 (40,

[M+H]+); HRMS (FAB+) Found 405.05338; $C_{16}H_{14}N_6O_3SCl$ requires 405.053663

4-Bromo-3-hydroxybenzoic acid

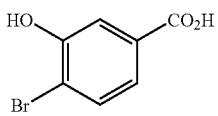

The title compound was prepared according to the method reported by Buehler et al.[Buehler, 1946] using 3-hydroxybenzoic acid (18.2 g, 132.0 mmol) and $Br_2$ (6.76 mL, 132.0 mmol) in glacial AcOH (250 mL) to give 4-bromo-3-hydroxybenzoic acid as a colourless crystalline solid (3.43 g, 12%) after recrystallisation from $Et_2O$/n-hexane; mp. 225-226° C. (lit.[Beyer, 1921] 227-228° C.); $\delta_H$ (270 MHz, DMSO-$d_6$) 7.28 (dd, J=8.2, 2.0, 1H), 7.51 (d, J=1.7, 1H), 7.60 (d, J=10.66 (bs, 1H,—exchanges with $D_2O$, ArOH) and 13.04 (bs, 1H—exchanges with $D_2O$, ArCOOH); LRMS (FAB+) m/z (rel. intensity) 218 (94, $[C_7H_5{}^{81}BrO_3+H]$), 216 (100, $[C_7H_5{}^{79}BrO_3+H]$); LC-MS (APCI-): $t_R$=1.38 min, m/z 216.78 (M–H); HPLC: $t_R$=1.35 min (100%); HRMS Found 218.94656; $C_7H_6{}^{81}BrO_3$ requires 218.94798.

Buehler et al., *J. Am. Chem. Soc.* 1946, 68, 574-577.

Methyl 4-bromo-3-hydroxybenzoate

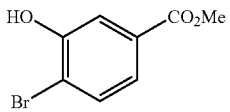

The title compound was prepared according to the method reported by Faltis et al.[Faltis, 1941] using 4-bromo-3-hydroxybenzoic acid (5.7 g, 26.26 mmol) and concentrated sulphuric acid (98% solution, 1.4 mL, 26.26 mmol) in anhydrous MeOH (150 mL) to give methyl 4-bromo-3-hydroxybenzoate as a colourless crystalline powder (5.4 g, 89%) after recrystallisation from MeOH; mp. 126-127° C., lit.[Faltis, 1941] (hexane) 124-125° C.; $\delta_H$ (270 MHz, $CDCl_3$) 3.90 (s, 3H), 5.75 (bs, 1H—exchanges with $D_2O$), 7.46 (dd, J=8.4, 2.0, 1H), 7.53 (d, J=8.2, 1H), 7.67 (d, J=1.7, 1H); LRMS (FAB+) m/z (rel. intensity) 232.0 (94, $[C_8H_7{}^{81}BrO_3+H]$), 230.8 (100, $[C_8H_7{}^{79}BrO_3+H]$); LC-MS (APCI-): $t_R$=3.72 min, m/z 230.96 (M–H); HPLC: $t_R$=2.04 min (99%); HRMS (FAB+) Found 232.96325; $C_8H_8O_3{}^{81}Br$ requires 232.96363.

Faltis et al., *Chem. Ber.*, 1941, 74, 79, 84

Methyl 4-bromo-3-(tetrahydropyran-2-yloxy)benzoate

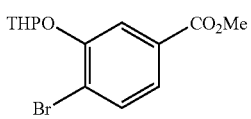

The title compound was prepared by adapting the method reported by Kita et al.[Kita, 1994] To a solution of methyl 4-bromo-3-hydroxybenzoate (4.0 g, 17.31 mmol) in anhydrous $CH_2Cl_2$ (30 mL) was added 3,4-dihydro-2H-pyran (3.95 mL, 43.28 mmol) and p-toluenesulfonic acid (0.01 g, 0.17 mmol) at 0° C. The mixture was stirred at this temperature for 90 min, warmed to room temperature and quenched with saturated $NaHCO_3$ solution (50 mL). The organic layer was separated, dried ($Na_2SO_4$) and concentrated in vacuo. The pale yellow residue was purified by flash column chromatography [$SiO_2$, $Et_2O$/n-hexane (4:6)] affording a colourless oil. The oil solidified on standing at room temperature to give methyl 4-bromo-3-(tetrahydropyran-2-yloxy)benzoate as colourless needles (4.12 g, 76%); $\delta_H$ (270 MHz, $CDCl_3$) 1.59-1.77 (m, 3H), 1.86-2.13 (m, 3H), 3.6-3.64 (m, 1H), 3.8-3.85 (m, 1H), 3.88 (s, 3H), 5.6-5.62 (m, 1H), 7.52 (dd, J=8.2, 1.7, 1H), 7.59 (d, J=8.4, 1H), 7.76 (d, J=2.0, 1H); LRMS (FAB+) m/z (rel. intensity) 316.9 (30, $[C_{13}H_{15}{}^{81}BrO_4+H]$]), 314.9 (47, $[C_{13}H_{15}{}^{79}BrO_4+H]$; LC-MS (APCI+):$t_R$=1.48 min, m/z 334.13 ($C_{13}H_{15}{}^{81}BrO_4+H_3O^+$), 332.11 ($C_{13}H_{15}{}^{79}BrO_4+H_3O^+$); HPLC: $t_R$=3.21 min (98%); HRMS (FAB+) Found 317.02290; $C_{13}H_{16}{}^{81}BrO_4$ requires 317.02115.

Kita et al., *Chem. Pharm. Bull.*, 1994, 42 (1), 147-150.

4-Bromo-3-(tetrahydropyran-2-yloxy)benzyl alcohol

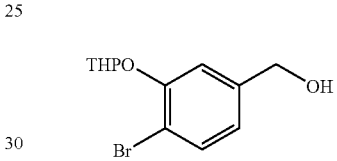

To a suspension of $LiAlH_4$ (0.72 g, 19.04 mmol) in anhydrous $Et_2O$ (90 mL) was slowly added a solution of methyl 4-bromo-3-(tetrahydropyran-2-yloxy)benzoate (4.0 g, 12.69 mmol) in anhydrous $Et_2O$ (10 mL). The mixture was stirred at room temperature for 2 h and then cautiously quenched with $Na_2SO_4.10H_2O$ (until gas evolution ceases). The solids were filtered off and washed with $Et_2O$ (100 mL). The combined organic fractions were then dried ($Na_2SO_4$) and concentrated in vacuo. The pale yellow residue was purified by flash column chromatography [$SiO_2$, $Et_2O$/n-hexane (7:3)] to give 4-bromo-3-(tetrahydropyran-2-yloxy)benzyl alcohol as a colourless oil (3.21 g, 88%). $\delta_H$ (270 MHz, $CDCl_3$) 1.54-1.76 (m, 3H), 1.82-2.12 (m, 3H), 3.54-3.64 (m, 1H), 3.8-3.94 (m, 1H), 4.61 (d, J=4.9, 2H), 5.52 (m, 1H), 6.85 (dd, J=7.9, 1.5, 1H), 7.13 (d, J=2.0, 1H), 7.49 (d, J=7.9, 1H), Nb. $ArCH_2OH$ too broad to be observed; LC-MS (APCI+): $t_R$=3.84 min, m/z 306.11 ($C_{12}H_{15}{}^{81}BrO_4+H_3O^+$), 304.13 ($C_{12}H_{15}{}^{79}BrO_4+H_3O^+$); HPLC: $t_R$=2.34 min (96%); HRMS (FAB+) Found 289.02646; $C_{12}H_{16}O_3{}^{81}Br$ requires 289.02624.

4-Bromo-3-(tetrahydropyran-2-yloxy)benzyl bromide

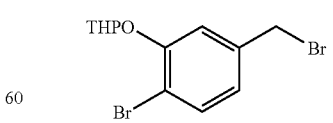

The title compound was prepared adapting the method reported by Wada et al.[Wada, 1979] with the following modifications. To a solution of 4-bromo-3-(tetrahydropyran-2-yloxy)benzyl alcohol (3.0 g, 10.45 mmol), carbon tetrabromide (6.93 g, 20.90 mmol) and anhydrous pyridine (0.85 mL, 10.45 mmol) in anhydrous Et$_2$O (50 mL) at 0° C. was added dropwise a solution of triphenylphosphine (5.48 g, 20.90 mmol) in anhydrous Et$_2$O (10 mL). The mixture was stirred at 0° C. for 1 h and then at room temperature overnight. The solvent was removed in vacuo and the residue suspended in n-hexane and filtered. The filtered solid was washed with n-hexane and the combined filtrates concentrated in vacuo to ca. 10 mL. The residue was purified by flash column chromatography [SiO$_2$, EtOAc/n-hexane (5:95)] to give 4-bromo-3-(tetrahydropyran-2-yloxy)benzyl bromide as a pale yellow oil (2.82 g, 77%) which slowly darkened on exposure to light and air; ¤$_H$ (270 MHz, CDCl$_3$) 1.58-2.12 (m, 6H), 3.58-3.65 (m, 1H), 3.83-3.92 (m, 1H), 4.41 (d, J=12.6, 2H), 5.53 (m, 1H), 6.89 (dd, J=7.9, 2.0, 1H), 7.16 (d, J=2.2, 1H), 7.48 (d, J=8.2, 1H); LC-MS (APCI−): t$_R$=4.71 min, m/z 266.95 (48, C$_{12}$H$_{14}$$^{81}$Br$_2$O$_4$—C$_5$H$_8$O—H), 264.93 (100, C$_{12}$H$_{14}$Br$_2$O$_4$—C$_5$H$_8$O—H), 262.92 (50, C$_{12}$H$_{14}$$^{79}$Br$_2$O$_4$—C$_5$H$_8$O—H); HPLC: t$_R$=3.91 min (94%)

Wada et al., *J. Chem. Soc.* (*Perkin Trans.* 1). 1979, 323-327.

4-[(3-(Tetrahydropyran-2-yloxy)-4-bromobenzyl)(4-cyanophenyl)amino]-4H-[1,2,4]triazole

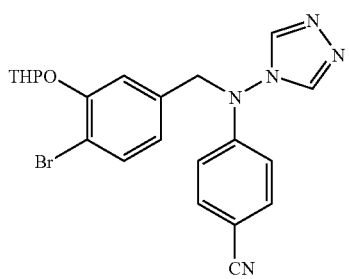

The title compound was prepared by adapting the method for 4-[(3-benzyloxybenzyl)(4-cyanophenyl)amino]-4H-[1,2,4]triazole using the following modifications. To a stirred suspension of NaH (60% dispersion in oil, 0.27 g, 6.78 mmol) in anhydrous DMF (10 mL) was added a solution of 4-[(4-cyanophenyl)amino]-4H-[1,2,4]triazole (1.26 g, 6.78 mmol) in anhydrous DMF (5 mL) and the mixture stirred at r.t. for 0.5 h. A solution of 4-bromo-3-(tetrahydropyran-2-yloxy)benzyl bromide (2.61 g, 7.46 mmol) in anhydrous DMF (5 mL) was then added and the mixture heated at 80-90° C. for 3 h. The mixture was cooled, diluted with EtOAc (50 mL), washed with water (4×100 mL), brine (100 mL) and dried (Na$_2$SO$_4$). Concentration in vacuo and subsequent purification by flash column chromatography [SiO$_2$, EtOAc (100%)] gave 4-[(3-(tetrahydropyran-2-yloxy)-4-bromobenzyl)(4-cyanophenyl) amino]-4H-[1,2,4]triazole as a yellow oil (3.05 g, 99%); δ$_H$ (270 MHz, CDCl$_3$) 1.61-1.99 (m, 6H), 3.55-3.59 (m, 1H), 3.73 (m, 1H), 4.75 (d, J=14.6, 1H), 4.90 (d, J=14.6, 1H), 5.41 (m, 1H), 6.64 (AA'BB', 2H), 6.69 (dd, J=8.2, 2.2, 1H), 7.00 (d, J=2.2, 1H), 7.49 (d, J=7.9, 1H), 7.57 (AA'BB', 2H), 8.15 (s, 2H); LRMS (FAB+) m/z (rel. intensity) 456.1 (54, [C$_{21}$H$_{20}$N$_5$O$_2$$^{81}$Br+H]), 454.1 (54, [C$_{21}$H$_{20}$N$_5$O$_2$$^{79}$Br+H]); LC-MS (APCI+): t$_R$=2.0 min, m/z 456.1 (94, [C$_{21}$H$_{20}$N$_5$O$_2$$^{81}$Br+H]), 454.1 (100, [C$_{21}$H$_{20}$N$_5$O$_2$$^{79}$Br+H]); HPLC: t$_R$=2.21 min (94%); HRMS (FAB+): Found 454.08627 C$_{21}$H$_{21}$N$_5$O$_2$$^{79}$Br requires 454.08786.

4-[(4-Bromo-3-hydroxybenzyl)(4-cyanophenyl) amino]-4H-[1,2,4]triazole (STX1216)

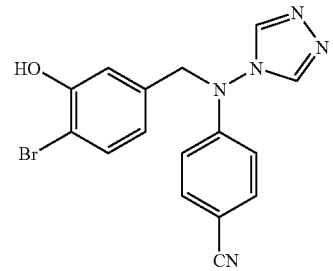

The title compound was prepared by adapting the method reported by Tafi et al.[Tafi,2002] with the following modifications. To a solution of 4-[(3-(tetrahydropyran-2-yloxy)-4-bromobenzyl)(4-cyanophenyl)amino]-4H-[1,2,4]triazole (3.05 g, 6.71 mmol) in MeOH (60 mL) was added a catalytic amount of p-toluenesulfonic acid at 0° C. and the mixture was stirred (allowing to slowly warm to room temperature) overnight. The solvent was removed in vacuo and the residue dissolved in EtOAc (100 mL). The organic fraction was washed with Na$_2$CO$_3$ solution (1M aqueous solution, 3×50 mL), brine (3×50 mL) and dried (Na$_2$SO$_4$). The solvent was removed in vacuo and the pale yellow residue recrystallised from EtOH to give STX1216 as an off-white powder (1.48 g, 60%); δ$_H$ (400 MHz, DMSO-d$_6$) 5.00 (s, 2H), 6.72 (dd, J=8.3, 2.1, 1H), 6.76 (AA'BB', 2H), 6.86 (d, J=1.8, 1H), 7.43 (d, J=8.0, 1H), 7.78 (AA'BB', 2H), 8.81 (s, 2H), 10.32 (s, 1H—exchanges with D$_2$O); δ$_C$ (100 MHz, DMSO-d$_6$) 57.08 (CH$_2$), 103.32, 109.42 114.07 (2×CH), 116.66 (CH), 119.51 (CH), 120.90 (CH), 133.54 (2×CH), 134.45 (2×CH), 136.14, 143.90, 151.82, 154.60; LRMS (FAB+) m/z (rel. intensity) 372.1 (94, [C$_{16}$H$_{12}$N$_5$O$^{81}$Br+H], 370.1 (100, [C$_{16}$H$_{12}$N$_5$O$^{79}$Br+H]); LC-MS (ES−) T$_R$=1.98 min, m/z 368.1 (C$_{16}$H$_{12}$N$_5$O$^{79}$Br—H), 370.1 (C$_{16}$H$_{12}$N$_5$O$^{81}$Br—H); HPLC t$_R$=1.77 min (100%); HRMS (FAB+) Found 372.02789; C$_{16}$H$_{13}$N$_5$O$^{81}$Br requires 372.02830. Found: C, 51.6; H, 3.4; N, 18.9; C$_{16}$H$_{12}$N$_5$OBr requires C, 51.9; H, 3.3; N, 18.9%.

Tafi et al, *J. Med. Chem.*, 2002, 45 (13), 2720-2732.

4-[(4-Bromo-3-O-sulfamoylbenzyl)(4cyanophenyl) amino]-4H-[1,2,4]triazole (STX1217)

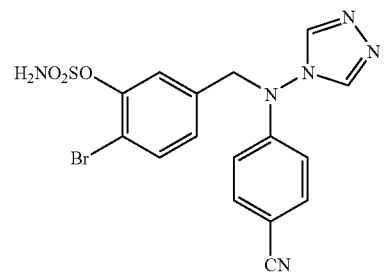

The title compound was sulfamoylated adapting the method for STX334 using STX1216 (0.5 g, 1.35 mmol) and sulfamoyl chloride (0.69 M solution toluene, 19.6 mL, 13.5 mmol) in anhydrous DMA (5 mL) to give STX1217 as an off-white solid (0.39 g, 64%) after chromatography [SiO$_2$, EtOAc (100%)]; $\delta_H$ (400 MHz, DMSO-d$_6$) 5.11 (s, 2H), 6.77 (AA'BB', 2H), 7.21 (dd, J=8.1, 1.8), 7.49 (d, J=2.1, 1H), 7.70 (d, J=8.1, 1H), 7.80 (AA'BB', 2H), 8.34 (br s, 2H—exchanges with D$_2$O), 8.85 (s, 2H); $\delta_C$ (400 MHz, DMSO-d6) 56.82 (CH$_2$), 103.52, 114.13 (2×CH), 115.90, 123.59 (CH), 128.18 (CH), 134.30 (CH), 134.49 (2×CH), 136.83, 143.81 (2×CH), 147.94, 151.71; LRMS (FAB+) m/z (rel. intensity) 451.9 (100, [C$_{16}$H$_{13}$N$_6$SO$_3$$^{81}$Br+H]), 449.9 (98, [C$_{16}$H$_{13}$N$_6$SO$_3$$^{79}$Br+H]); LC-MS (APCI+) t$_R$=3.01 min, m/z 449 (100, [C$_{16}$H$_{13}$N$_6$SO$_3$$^{79}$Br+H]), 451 (83, [C$_{16}$H$_{13}$N$_6$SO$_3$$^{81}$Br+H]); HPLC t$_R$=1.67 min (100%); Found: C, 43.0; H, 3.0; N, 18.5; C$_{16}$H$_{13}$N$_6$SO$_3$Br requires C, 42.8; H, 2.9; N, 18.7%.

4-[(3-Benzyloxy-4-methoxybenzyl)(4-cyanophenyl) amino]-4H-[1,2,4]triazole

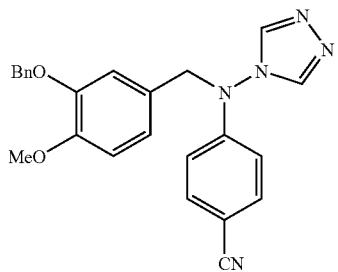

The title compound was prepared by adapting the method for 4-[(3-benzyloxybenzyl)(4-cyanophenyl)amino]-4H-[1,2,4]triazole using NaH (60% dispersion in oil, 0.22 g, 5.4 mmol), 4-[(4-cyanophenyl)amino]-4H-[1,2,4]triazole (1.0 g, 5.68 mmol) and 4-methoxy-3-benzyloxybenzyl bromide[Meyers, 1989] (1.66 g, 5.4 mmol) in anhydrous DMF (5 mL) to give 4-[(3-benzyloxy-4-methoxybenzyl)(4-cyanophenyl)amino]-4H-[1,2,4]triazole as an off-white solid (0.97 g, 44%) after recrystallisation; mp. 138-141° C.; $\delta_H$ (400 MHz, CDCl$_3$) 3.89 (s, 3H), 4.72 (s, 2H), 5.12 (s, 2H), 6.59 (AA'BB', 2H), 6.62 (d, J=2, 1H), 6.64 (dd, J=7.8, 2, 1H), 6.79 (d, J=7.8, 1H), 7.28-7.34 (m, 5H), 7.57 (AA'BB', 2H), 7.74 (s, 2H); LRMS (FAB+) m/z (rel. intensity) 412 (100, [M+H]), 343 (51), 227 (72%); HPLC: t$_R$=2.21 min (94%); HRMS (FAB+): Found 412.1774 C$_{24}$H$_{22}$N$_5$O$_2$ requires 412.1776.

Meyer et al., *Heterocycles.* 1989, 28 (1), 295-301.

4-[(3-Hydroxy-4-methoxybenzyl)(4-cyanophenyl) amino]-4H-[1,2,4]triazole (STX363)

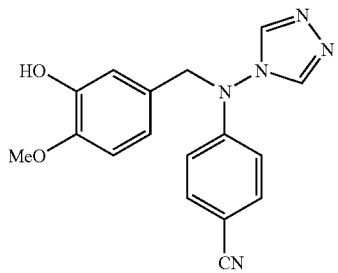

The title compound was hydrogenated (over 16 h) by adapting the method for STX333 using 4-[(3-benzyloxy-4-methoxybenzyl)(4-cyanophenyl)amino]-4H-[1,2,4]triazole (0.411 g, 0.999 mmol) and Pd—C (10% by wt., 0.042 g) in THF/MeOH (1:1) (20 mL) to give STX363 as a colourless powder (0.164 g, 51%) after recrystallisation; $\delta_H$ (400 MHz, DMSO-d$_6$) 3.71 (s, 3H); 4.88 (s, 2H), 6.62 (dd, J=8.2, 1.95, 1H), 6.68 (d, J=1.95, 1H), 6.74 (AA'BB', 2H), 6.80 (d, J=8.2, 1H), 7.74 (AA—BB—, 2H), 8.70 (s, 2H), 9.00 (s, 1H—exchanges with D2O); LRMS (FAB+) m/z (rel. intensity) 322 (100, [M+H]), 253 (61%); HPLC t$_R$=2.03 min (99% purity); HRMS (FAB+) Found 322.1304; C$_{17}$H$_{16}$N$_5$O$_2$ requires 322.1304.

4-[(4-Methoxy-3-O-sulfamoylbenzyl)(4-cyanophenyl)amino]-4H-[1,2,4]triazole (STX661)

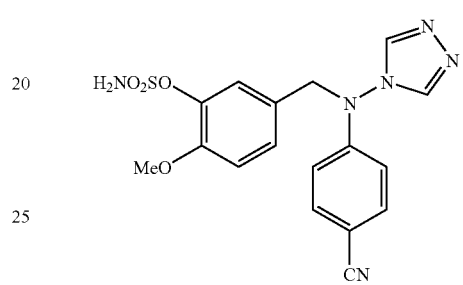

The title compound was sulfamoylated adapting the method for STX334 using STX363 (0.1 g, 0.31 mmol) and sulfamoyl chloride (0.69 M solution toluene, 2.71 mL, x.xx mmol) in anhydrous DMA (2 mL) to give STX661 as a colourless solid (0.04 g, 32%) after precipitation from EtOAc solution by addition of n-hexane; $\delta_H$ (400 MHz, DMSO-d$_6$) 3.77 (s, 3H), 5.00 (s, 2H), 6.77 (AA'BB', 2H), 7.06 (d, J=8.6, 1H), 7.11 (dd, J=8.6, 2.3, 1H), 7.27 (d, J=2.3, 1H), 7.77 (AA'BB', 2H), 7.94 (s, 2H—exchanges with D$_2$O, 8.75 (s, 2H); LC-MS (APCI+) t$_R$=4.70 min (M+H=401); HPLC t$_R$=2.04 min (98% purity).

4-[(2-Bromo-ethyl)-[1,2,4]triazol-4-yl-amino]-benzonitrile (CAB03031)

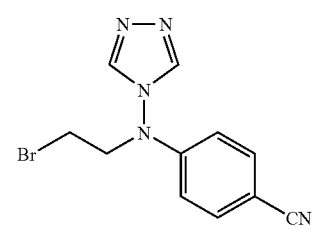

Sodium hydride (240 mg, 6.0 mmol) was added to a solution of 4-([1,2,4]triazol-4-ylamino)-benzonitrile (926 mg, 5.0 mmol) in DMSO (25 ml) at r.t. The mixture was stirred for 1 hour at this temperature and 1,2-dibromethane (5 ml) was added. The reaction mixture was stirred overnight and ethyl acetate (100 ml) was added. The mixture was transferred into a separation funnel and extracted with water (twice 100 ml) and brine (20 ml). The organic layer was dried over sodium sulphate and concentrated under reduced pressure (water bath temperature <30° C.). The resulting orange oil was mixed with diethyl ether (100 ml) and filtered through a layer of silica (ca. 5 cm). The silica was washed with more diethyl ether (ca. 100 ml) to remove the excess of 1,2-dibromoethane; the crude product was washed from the silica with acetone (120 ml). The acetone solution was concentrated under reduced pressure and the residue was purified by column-chromatography (eluent: ethyl acetate) to give the title compound as a white solid. Yield: 628 mg (43%). $^1$H-NMR (400 MHz, d6-DMSO) δ=3.61 (t, J=6.2 Hz, 2H), 4.30 (t, J=6.4 Hz, 2H), 6.64 (d, J=9.0 Hz), 7.74 (d, 9.0 Hz, 2H), 8.97 (s, 2H). LRMS (FAB+):292.0 (100, [M+H]$^+$)

4-{[2-(3-Hydroxy-phenylsulfanyl)-ethyl]-[1,2,4]triazol-4-yl-amino}-benzonitrile (CAB02149, STX512)

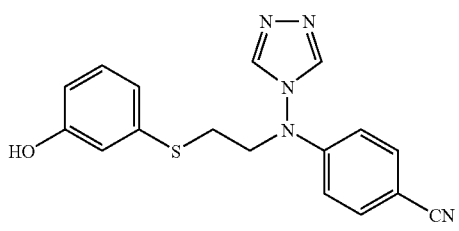

A mixture of 4-[(2-Bromo-ethyl)-[1,2,4]triazol-4-yl-amino]-benzonitrile (CAB02148=CAB03031, 146 mg, 0.50 mmol), 3-(tert-butyl-dimethylsiloxy)-thiophenol (240 mg, 1.0 mmol) and potassium carbonate (276 mg, 2.0 mmol) in DMF (10 ml) was stirred for 48 hours at room temperature. The mixture was transferred into a separation funnel and ethyl acetate (50 ml) and water (50 ml) were added. The organic layer was separated, washed with brine (30 ml), dried over sodium sulphate and concentrated under reduced pressure. The residue was crystallised from methanol. Yield: 93 mg (55%) colourless crystals (STX512). $^1$H-NMR (400 MHz, d6-DMSO) δ=3.14 (t, J=7.0 Hz, 2H), 4.02 (t, J=7.0 Hz, 2H), 6.53 (d, J=9.0 Hz, 2H), 6.62 (ddd, J=7.8, 2.0, 0.8 Hz, 1H), 6.70-6.72 (m, 2H), 7.10 (dd, J=7.8, 7.8, 1H), 7.70 (d, J=9.0 Hz, 2H), 8.94 (s, 2H), 9.60 (s, 1H, —OH). $^{13}$C-NMR (100 MHz, d6-DMSO) δ=29.53 52.46, 102.38, 112.86, 113.57, 115.36, 119.00, 130.11, 133.94, 135.82, 143.50, 150.71, 157.90, 169.59. LRMS (FAB+): 338.2 (100, [M+H]$^+$). C$_{17}$H$_{15}$N$_5$OS (337.4) Calculated: C, 60.52% H, 4.48% N, 20.76%, Found: C, 60.6% H, 4.53% N, 20.8%.

Sulfamic Acid 3-{2-[(4-cyano-phenyl)-[1,2,4]triazol-4-yl-amino]-ethylsulfanyl}-phenyl ester (CAB03131, STX1014)

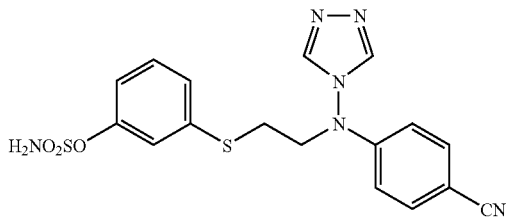

Sulphamoyl chloride solution in toluene (1.5 ml, 0.7 M, 1.05 mmol) was concentrated under reduced pressure (30° C. water bath temperature) to ca. 0.5 ml volume. The residue was cooled to 0° C. (ice bath) and N,N-dimethyl acetamide (5 ml) was added. 4-{[2-(3-Hydroxy-phenylsulfanyl)-ethyl]-[1,2,4]triazol-4-yl-amino}-benzonitrile (CAB02149, 75 mg, 0.22 mmol) was added to the colourless solution and the mixture was stirred for 18 hours at room temperature. Ethyl acetate (50 ml) and water (50 mL) were added to the solution, the organic layer was separated, washed with water (2×30 ml) and brine (1×20 ml), dried over sodium sulphate and concentrated under reduced pressure. The residue was dissolved in a small amount of acetone and precipitated by addition of hexane. The precipitate (STX1014) was filtered off and dried under high vacuum. Yield: 79 mg (85%) light yellow powder. $^1$H-NMR (400 MHz, DMSO-d$_6$) δ3.23 (t, J=7.0 Hz, 2H), 4.07 (t, J=7.0 Hz, 2H), 6.54 (d, J=8.9 Hz, 2H), 7.08-7.12 (m, 1H), 7.20-7.26 (m, 1H), 7.39 (dd, J=9.2, 9.2 Hz, 1H), 7.69 (d, J=8.9 Hz, 2H), 8.03 (s, 2H, —NH$_2$), 8.94 (s, 2H); MS (FAB+): m/z 85.1.1 (28%), 417.0 (100%, [C$_{17}$H$_{16}$N$_6$O$_3$S$_2$+H]$^+$); HRMS (FAB+) for C$_{17}$H$_{17}$N$_6$O$_3$S$_2$: 417.08036; Found, 417.08067; HPLC t$_R$=1.53 min (99.7%).

tert-Butyl-(3-chloromethylsulfanyl-phenoxy)-dimethyl-silane

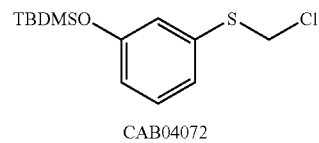

CAB04072

DBU (914 mg, 6.0 mmol) was added to a solution of 3-(tert-Butyl-dimethyl-silanyloxy)-benzenethiol (1.00 g, 4.16 mmol) in bromo-chloro methane (5 ml) at room temperature. Stirring was continued for 2 hours and Et$_2$O (50 ml) and 2M KHSO$_4$ (30 ml) were added. The organic layer was separated, washed with 2M KHSO$_4$ (30 ml) and brine (30 ml), dried (Na$_2$SO$_4$) and concentrated under reduced pressure. The resulting oil was analysed by $^1$H-NMR spectroscopy and was used without further purification. Yield: 1.01 g (84%).
$^1$H-NMR (270 MHz, DMSO-d$_6$) δ0.21 (6H, s, 2×SiCH$_3$), 0.99 (9H, s, —C(CH$_3$)$_3$), 4.97 (2H, s, —CH$_2$Cl), 6.70-7.30 (m, 4H).

4-[(3-Hydroxy-phenylsulfanylmethyl)-[1,2,4]triazol-4-yl-amino]-benzonitrile

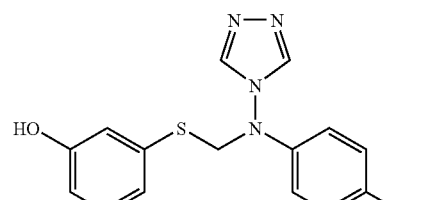

CAB04074 STX1349)

NaH (140 mg, 3.50 mmol, 60% in mineral oil) was added to a solution of 4-([1,2,4]Triazol-4-ylamino)-benzonitrile (648 mg, 3.50 mmol) in DMF. The mixture was stirred for one hour at r.t. and a solution of CAB04072 (1.01 g, 3.50 mmol) in DMF (10 ml) was added. Stirring was continued for 24 hours, EtOAc (75 ml) and water (50 ml) were added, the organic layer was separated, washed with water (3×30 ml)

and brine (30 ml), dried (Na$_2$SO$_4$) and concentrated under reduced pressure. The residue was purified by flash chromatography (EtOAc, R$_f$: 0.30) to give the title compound as a white solid. Yield: 136 mg (12%).

m.p.: 188-190° C.;

$^1$H-NMR (270 MHz, DMSO-d$_6$) δ5.62 (2H, s), 6.64 (2H, d, J=9.0 Hz,), 7.20-7.26 (1H, m) 7.35-7.50 (3H, m), 7.74 (2H, d, 9.0 Hz), 8.81 (2H, s), 9.75 (1H, s, —OH);

MS (FAB+): m/z 324.0 (100%, [C$_{16}$H$_{14}$N$_5$OS]$^+$), 255.0 (85%);

HRMS (FAB+) calcd. for C$_{16}$H$_{14}$N$_5$OS:324.09191; found, 324.09173.

Sulfamic acid 3-{[(4-cyano-phenyl)-[1,2,4]triazol-4-yl-amino]-methylsulfanyl}-phenyl ester

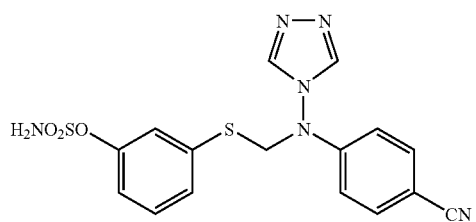

CAB04086 (STX1351)

Sulfamoyl chloride solution in toluene (1.5 ml, 0.7 M, 1.05 mmol) was concentrated under reduced pressure. The residue was cooled to 0° C. (icebath) and DMA (5 ml) was added slowly. CAB04074 (97 mg, 0.30 mmol) was added to the colourless solution and the mixture was stirred for 18 h at room temperature. EtOAc (50 ml) and water (50 ml) were added, the organic layer was separated, washed with water (2×30 ml) and brine (20 ml), dried over Na$_2$SO$_4$ and concentrated under reduced pressure. The residue was dissolved in a small amount of acetone and precipitated by addition of Et$_2$O. The precipitate was filtered of and dried under high vacuum. Yield 76 mg (63%).

m.p.: 167-170° C. (dec.);

$^1$H-NMR (270 MHz, DMSO-d$_6$) δ5.64 (2H, s), 6.66 (2H, d, J=9.0 Hz,), 7.16-7.20 (1H, m), 7.30-7.44 (3H, m), 7.71 (2H, d, 9.0 Hz), 8.05 (2H, s, —NH$_2$), 8.77 (2H, s);

MS (FAB+): m/z 403.0 (100%, [C$_{16}$H$_{15}$N$_6$O$_3$S$_2$]$^+$);

HRMS (FAB+) calcd. for C$_{16}$H$_{15}$N$_6$O$_3$S$_2$: 403.06471; found, 403.06623

Biological Data

Compounds were tested for aromatase and steroid sulphatase inhibition in accordance with the above Protocols. Each compound in accordance with the present invention is found to inhibit steroid sulphatase and aromatase.

The following in vitro data were recorded. IC50 values are shown as just numbers (without units). Compounds for which % Inhibition at 10 micromolar was measured this is denoted with a % sign.

A) Compounds of Formula III

| Compound | Structure | JEG3 cells IC$_{50}$ Aromatase (nM) or % inhibition @ 10 μM | JEG3 cells IC$_{50}$ Sulfatase (nM) or % inhibition @ 10 μM |
|---|---|---|---|
| STX334 | 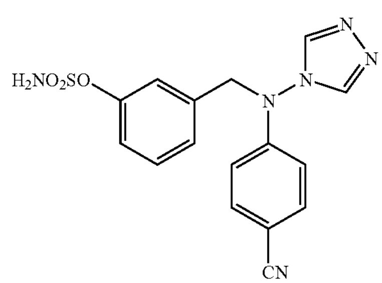 | IC50 39 ± 10.1 | IC50 5133 ± 65.4 |
| STX1122 | 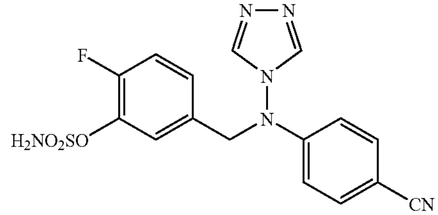 | IC50 0.77 ± 0.03 | IC50 590 |

| Compound | Structure | JEG3 cells IC$_{50}$ Aromatase (nM) or % inhibition @ 10 μM | JEG3 cells IC$_{50}$ Sulfatase (nM) or % inhibition @ 10 μM |
|---|---|---|---|
| STX559 | 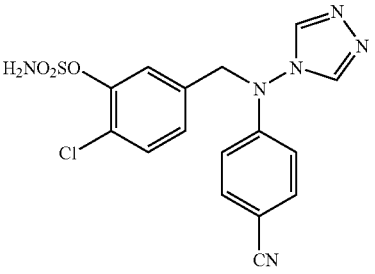 | IC50 0.92 | IC50 >10,000 |
| STX1217 | 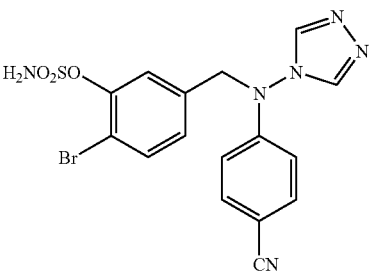 | IC50 3.9 ± 0.9 | IC50 >10,000 |
| STX661 | 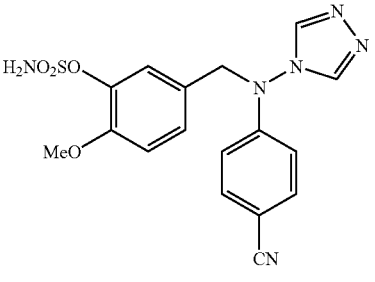 | IC50 12 | 12 ± 3.1% |
| STX1014 | 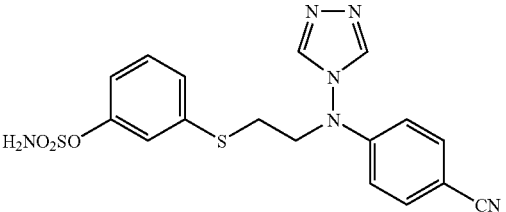 | IC50 1.7 ± 0.5 | IC50 >10,000 |
| STX1351 | 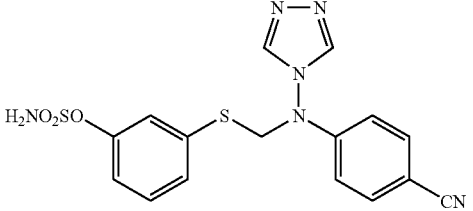 | IC50 3.9 ± 1.8 | IC50 3500 ± 100 |

B) Compounds of Formula IV

| Compound | Structure | JEG3 cells $IC_{50}$ Aromatase (nM) or % inhibition @ 10 μM | JEG3 cells $IC_{50}$ Sulfatase (nM) or % inhibition @ 10 μM |
|---|---|---|---|
| STX1001 | H₂NO₂SO—C₆H₄—CH(triazolyl)—C₆H₄—OSO₂NH₂ (3,3'-substituted) | IC50 99 ± 0.01 | 31.4% |
| STX1007 | H₂NO₂SO—C₆H₃(OMe)—CH(triazolyl)—C₆H₃(OMe)—OSO₂NH₂ | 40% | 10.9% |

Data from WO 03/045925 are presented below. Set out are inhibitory data for five compound which correspond to the "para" equivalents of a number of the above meta compounds.

| Compound | Structure | AROMATASE $IC_{50}$ (nM) | SULPHATASE $IC_{50}$ (nM) |
|---|---|---|---|
| STX258 | H₂N-SO₂-O—C₆H₄—CH₂—N(triazolyl)—C₆H₄—CN | 100 | 227 |
| STX268 | H₂N-SO₂-O—C₆H₄—CH(triazolyl)—C₆H₄—O-SO₂-NH₂ | 3044 | >10000 (31% at 10 μM) |

-continued

| Compound | Structure | AROMATASE IC$_{50}$ (nM) | SULPHATASE IC$_{50}$ (nM) |
|---|---|---|---|
| STX681 | 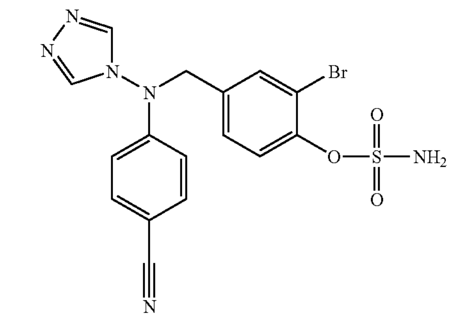 | 0.82 | 39 |
| STX694 | 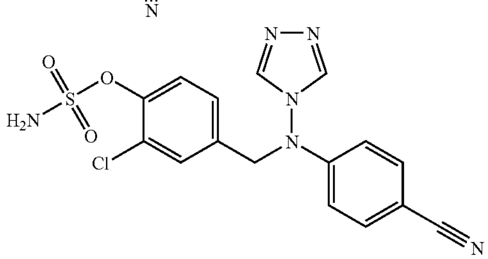 | 2.3 | 20 |
| STX700 | 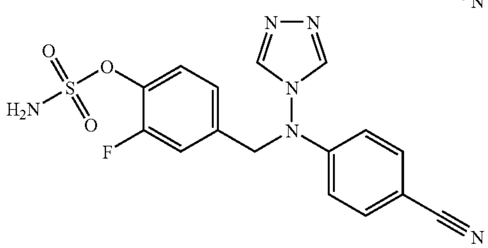 | 12 | 40 |

The data for the two sets of compounds are compared below:

| Meta or Para | Compound | AROMATASE IC$_{50}$ (nM) or % inhibition @ 10 μM | SULPHATASE IC$_{50}$ (nM) or % inhibition @ 10 μM |
|---|---|---|---|
| Meta | STX334 | 39 ± 10.1 | 5133 ± 65.4 |
| Para | STX258 | 100 | 227 |
| Meta | STX 1001 | 99 ± 0.01 | 31.4% |
| Para | STX 268 | 3044 | >10,000 (31% at 10 uM) |
| Meta | STX 1217 | 3.9 ± 0.9 | >10,000 |
| Para | STX 681 | 0.82 | 39 |
| Meta | STX 559 | 0.92 | >10,000 |
| Para | STX 694 | 2.3 | 20 |
| Meta | STX 1122 | 0.77 ± 0.03 | 590 |
| Para | STX 700 | 12 | 40 |

The invention will now be further described by the following numbered paragraphs:

i. A compound of Formula IV

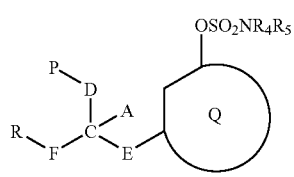

Formula IV wherein

A is selected from H, OH, halogen and hydrocarbyl

D, E and F are each independently of each other an optional linker group;

P, Q and R are independently of each other a ring system, wherein R$^4$ and R$^5$ are independently selected from H, alkyl, cycloalkyl, alkenyl, acyl and aryl, or combinations thereof, or together represent alkylene, wherein the or each alkyl or cycloalkyl or alkenyl or optionally contain one or more hetero atoms or groups.

ii. A compound according to paragraph i wherein at least one of the optional linker groups is present.

iii. A compound according to any one of the preceding paragraphs wherein only one of the optional linker groups is present.

iv. A compound according to any one of the preceding paragraphs wherein the optional linker groups are independently selected from C=O and hydrocarbyl groups.

v. A compound according to any one of the preceding paragraphs wherein the optional linker groups are independently selected from C=O and straight or branched hydrocarbon groups containing at least one hetero atom in the group.

vi. A compound according to any one of the preceding paragraphs wherein the optional linker groups are independently selected from C=O and hydrocarbon groups and a group of the formula

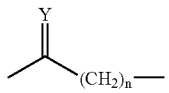

wherein n is 1 to 6 and Y=Oxygen, Sulphur or CH$_2$.

vii. A compound according to any one of the preceding paragraphs wherein the optional linker groups are independently selected from C=O and linear or branched hydrocarbon groups having a carbon chain of from 1 to 6 carbon atoms and a group of the formula

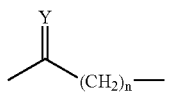

wherein n is 1 to 6 and Y=Oxygen, Sulphur or CH$_2$.

viii. A compound according to any one of the preceding paragraphs wherein E is selected from straight or branched hydrocarbon groups containing at least one hetero atom in the group.

ix. A compound according to any one of the preceding paragraphs wherein E is selected from hydrocarbon groups comprising at least 2 carbons and a group of the formula

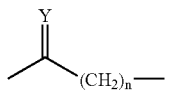

wherein n is 1 to 6 and Y=Oxygen, Sulphur or CH$_2$.

x. A compound according to any one of the preceding paragraphs wherein E is selected from linear or branched hydrocarbon groups having a carbon chain of from 2 to 6 carbon atoms and a group of the formula

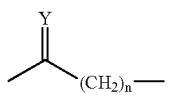

wherein n is 1 to 6 and Y=Oxygen, Sulphur or CH$_2$.

xi. A compound according to any one of the preceding paragraphs wherein P, Q and R are independently selected from or comprise an aromatic ring.

xii. A compound according to any one of the preceding paragraphs wherein P, Q and R are independently selected from substituted and unsubstituted aromatic rings.

xiii. A compound according to any one of the preceding paragraphs wherein P, Q and R are independently selected from ring systems comprising from 3 to 10 members.

xiv. A compound according to any one of the preceding paragraphs wherein P, Q and R are independently selected from ring systems comprising from 5, 6 or 7 members.

xv. A compound according to any one of the preceding paragraphs wherein P, Q and R are independently selected from ring systems comprising carbon and optionally one or more hetero atoms.

xvi. A compound according to any one of the preceding paragraphs wherein P, Q and R are independently selected from ring systems comprising carbon and optionally one, two or three hetero atoms.

xvii. A compound according to any one of the preceding paragraphs wherein at least one of P, Q and R is independently selected from ring systems comprising carbon and one or more hetero atoms.

xviii. A compound according to any one of the preceding paragraphs wherein at least one of P, Q and R is independently selected from ring systems comprising carbon and one or more hetero atoms selected from Nitrogen, Sulphur and Oxygen.

xix. A compound according to any one of the preceding paragraphs wherein one of P, Q and R is a ring system comprising carbon and one or more hetero atoms and two of P, Q and R are independently selected from carbocyclic ring systems.

xx. A compound according to any one of the preceding paragraphs wherein one of P, Q and R is a ring system comprising carbon and one or more hetero atoms selected from Nitrogen, Sulphur and Oxygen and two of P, Q and R are independently selected from carbocyclic ring systems.

xxi. A compound according to any one of the preceding paragraphs wherein one of P, Q and R is 4H-1,2,4-triazole or 1H-1,2,4-triazole and two of P, Q and R are independently selected from substituted or unsubstituted benzyl rings.

xxii. A compound according to any one of the preceding paragraphs of Formula IV wherein
D, E and F are not present
R is a triazole
P is a substituted or unsubstituted aryl group
Q is a substituted or unsubstituted aryl group xxiii. A compound according to paragraph xxii wherein R is 1H-1,2,4-triazole.

xxiv. A compound according to paragraph xxii or xxiii wherein P is a substituted or unsubstituted benzyl group.

xxv. A compound according to paragraph xxii, xxiii or xxiv wherein Q is a substituted or unsubstituted benzyl group xxvi. A compound according to paragraph i of Formula V

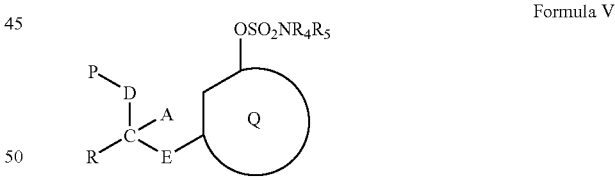

Formula V wherein
D and E are each independently of each other an optional linker group,
P, Q and R are independently of each other a ring system.

xxvii. A compound according to paragraph xxvi wherein one of P and Q is a ring system comprising carbon and one or more hetero atoms and the other of P and Q is a carbocyclic ring system.

xxviii. A compound according to paragraph xxvii wherein one of P and Q is a ring system comprising carbon and one or more hetero atoms selected from Nitrogen, Sulphur and Oxygen and the other of P and Q is a carbocyclic ring system.

xxix. A compound according to paragraph xxviii wherein one of P and Q is 4H-1,2,4-triazole and the other of P and Q is a substituted or unsubstituted benzyl ring.

xxx. A compound according to paragraph xxviii wherein P is 4H-1,2,4-triazole and Q is a substituted or unsubstituted benzyl ring.

xxxi. A compound according to any one of paragraphs i to xxx for use in medicine.

xxxii. A pharmaceutical composition comprising the compound according to any one of paragraphs i to xxx optionally admixed with a pharmaceutically acceptable carrier, diluent, excipient or adjuvant.

xxxiii. Use of a compound according to any one of paragraphs i to xxx in the manufacture of a medicament for use in the therapy of a condition or disease associated with STS and/or aromatase and/or cell cycling and/or apoptosis and/or cell growth.

xxxiv. Use of a compound according to any one of paragraphs i to xxx in the manufacture of a medicament for use in the therapy of a condition or disease associated with STS and aromatase.

xxxv. Use of a compound according to any one of paragraphs i to xxx in the manufacture of a medicament for use in the therapy of a condition or disease associated with adverse STS levels and/or adverse aromatase levels and/or cell cycling and/or apoptosis and/or cell growth.

xxxvi. Use of a compound according to any one of paragraphs i to xxx in the manufacture of a medicament for use in the therapy of a condition or disease associated with adverse STS levels and adverse aromatase levels.

xxxvii. Use of a compound according to any one of paragraphs i to xxx in the manufacture of a medicament for inhibiting STS activity and/or inhibiting aromatase activity.

xxxviii. Use of a compound according to any one of paragraphs i to xxx in the manufacture of a medicament for inhibiting STS activity and inhibiting aromatase activity.

xxxix. A compound as substantially hereinbefore described with reference to the Examples.

xl. A composition as substantially hereinbefore described with reference to the Examples.

xli. A method or use as substantially hereinbefore described with reference to the Examples.

All publications and patents and patent applications mentioned in the above specification are herein incorporated by reference. Various modifications and variations of the present invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry, biology or related fields are intended to be within the scope of the following claims.

The invention claimed is:

1. A compound of Formula IV

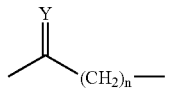

Formula IV

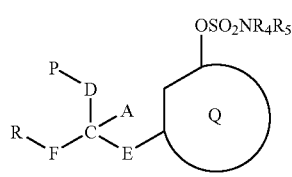

wherein
A is selected from H, OH, halogen and straight or branched $C_1$-$C_{10}$ hydrocarbon D, E and F are each independently of each other an optional linker group independently selected from C=O and hydrocarbon groups and a group of the formula

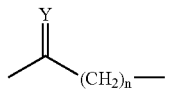

wherein n is 1 to 6 and Y=Oxygen, Sulphur or $CH_2$;

P, Q and R are independently of each other a ring system wherein one of P, Q and R is a ring system containing at least one carbon atom and one or more hetero atom and two of P, Q and R are independently selected from carbocylic ring systems substituted by one or more alkoxy groups, wherein $R^4$ and $R^5$ are independently selected from H, alkyl, cycloalkyl, alkenyl, acyl and aryl, or combinations thereof, or together represent alkylene, wherein each alkyl or cycloalkyl or alkenyl optionally contain one or more hetero atoms or groups.

2. A compound according to claim 1 wherein at least one of the optional linker groups is present.

3. A compound according to claim 1 wherein only one of the optional linker groups is present.

4. A compound according to claim 1 wherein the optional linker groups are independently selected from C=O and linear or branched hydrocarbon groups having a carbon chain of from 1 to 6 carbon atoms and a group of the formula

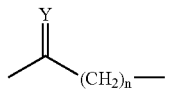

wherein n is 1 to 6 and Y=Oxygen, Sulphur or $CH_2$.

5. A compound according to claim 1 wherein E is selected from hydrocarbon groups having at least 2 carbons and a group of the formula

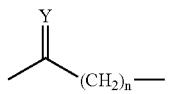

wherein n is 1 to 6 and Y=Oxygen, Sulphur or $CH_2$.

6. A compound according to claim 1 wherein E is selected from linear or branched hydrocarbon groups having a carbon chain of from 2 to 6 carbon atoms and a group of the formula

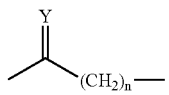

wherein n is 1 to 6 and Y=Oxygen, Sulphur or $CH_2$.

7. A compound according to claim 1 wherein one of P, Q and R is a ring system comprising carbon and one or more hetero atoms selected from Nitrogen, Sulphur and Oxygen and two of P, Q and R are independently selected from carbocylic ring systems.

8. A compound according to claim 1 wherein one of P, Q and R is 1H-1,2,4-triazole and two of P, Q and R are independently selected from substituted benzyl rings.

9. A compound according to claim 1 of Formula IV wherein D, E and F are not present; R is a triazole; P is a substituted aryl group; and Q is a substituted aryl group.

10. A compound according to claim 9 wherein R is 1H-1,2,4-triazole.

11. A compound according to claim 9 wherein P is a substituted benzyl group.

12. A compound according to claim 9 wherein Q is a substituted benzyl group.

13. A compound according to claim 1 of Formula V

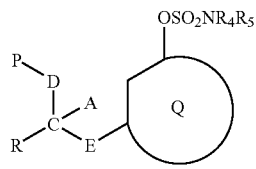

Formula V wherein
D and E are each independently of each other an optional linker group as defined in claim 1,
P, Q and R are independently of each other a ring system as defined in claim 1.

14. A compound according to claim 13 wherein one of P and Q is 1H-1,2,4-triazole and the other of P and Q is a substituted benzyl ring.

15. A compound according to claim 13 wherein P is 1H-1,2,4-triazole and Q is a substituted benzyl ring.

16. A compound according to claim 1 for use in the treatment of breast cancer.

17. A pharmaceutical composition comprising the compound according to claim 1 optionally admixed with a pharmaceutically acceptable carrier, diluent, excipient or adjuvant.

* * * * *